(12) United States Patent
Tsugo

(10) Patent No.: US 10,052,072 B2
(45) Date of Patent: Aug. 21, 2018

(54) DATA OUTPUT DEVICE AND METHOD, AND NON-TRANSITORY COMPUTER READABLE MEDIUM

(71) Applicant: FUJIFILM Corporation, Tokyo (JP)

(72) Inventor: Akinari Tsugo, Ashigarakami-gun (JP)

(73) Assignee: FUJIFILM Corporation, Tokyo (JP)

(*) Notice: Subject to any disclaimer, the term of this patent is extended or adjusted under 35 U.S.C. 154(b) by 0 days.

(21) Appl. No.: 15/279,534

(22) Filed: Sep. 29, 2016

(65) Prior Publication Data

US 2017/0014090 A1    Jan. 19, 2017

Related U.S. Application Data

(63) Continuation of application No. PCT/JP2015/057932, filed on Mar. 17, 2015.

(30) Foreign Application Priority Data

Mar. 31, 2014 (JP) ................. 2014-074276

(51) Int. Cl.
   *G06F 19/00*     (2018.01)
   *G09G 5/00*      (2006.01)
   (Continued)

(52) U.S. Cl.
   CPC ............ *A61B 5/7425* (2013.01); *A61B 5/00* (2013.01); *A61B 5/02055* (2013.01);
   (Continued)

(58) Field of Classification Search
   CPC ....... A61B 5/00; A61B 5/02055; A61B 5/021; A61B 5/024; A61B 5/0816; A61B 5/4836;
   (Continued)

(56) References Cited

U.S. PATENT DOCUMENTS 8,113,844 B2 *  2/2012  Huang ................. G09B 9/00
                                                   434/219
2008/0145830 A1  6/2008  Huang et al.
(Continued)

OTHER PUBLICATIONS

International Search Report, issued in PCT/JP2015/057932 (PCT/ISA/210), dated Jun. 16, 2015.
(Continued)

*Primary Examiner* — Sing-Wai Wu
(74) *Attorney, Agent, or Firm* — Birch, Stewart, Kolasch & Birch, LLP

(57) ABSTRACT

A data output device capable of simply performing both of recognition of an entire image at an important point in time regarding medical care and recognition of a detailed change in time series data at the point in time is provided.
A data display screen includes first and second display areas. In the first display area, time-series data indicating a state transition of a patient or content related to medical care performed on the patient is displayed in a graph. First indicators can be assigned to the graph. Second indicators are displayed at corresponding positions in the second display area that temporally correspond to designated positions in the first display area to which the first indicators are assigned. A second time axis in the second display area has a time scale which is longer than that of a first time axis in the first display area.

14 Claims, 30 Drawing Sheets

(51) Int. Cl.
    *G09G 5/18*     (2006.01)
    *A61B 5/00*     (2006.01)
    *A61B 5/0205*     (2006.01)
    *G06F 3/048*     (2013.01)
    *G06F 3/0485*     (2013.01)
    *G06Q 50/24*     (2012.01)
    *G06Q 10/10*     (2012.01)
    *G16H 40/63*     (2018.01)
    *G16H 15/00*     (2018.01)
    *A61B 5/021*     (2006.01)
    *A61B 5/024*     (2006.01)
    *A61B 5/08*     (2006.01)
    *G06F 3/0482*     (2013.01)
    *G06T 11/20*     (2006.01)

(52) U.S. Cl.
    CPC ............ *A61B 5/4836* (2013.01); *G06F 3/048* (2013.01); *G06F 3/0485* (2013.01); *G06F 19/3456* (2013.01); *G06Q 10/10* (2013.01); *G06Q 50/24* (2013.01); *G09G 5/006* (2013.01); *G09G 5/18* (2013.01); *G16H 15/00* (2018.01); *G16H 40/63* (2018.01); *A61B 5/021* (2013.01); *A61B 5/024* (2013.01); *A61B 5/0816* (2013.01); *G06F 3/0482* (2013.01); *G06F 2203/04803* (2013.01); *G06T 11/206* (2013.01); *G09G 2380/08* (2013.01)

(58) Field of Classification Search
    CPC ............... A61B 5/7425; G06F 19/3406; G06F 19/3456; G06F 19/3487; G06F 2203/04803; G06F 3/048; G06F 3/0482; G06F 3/0485
    See application file for complete search history.

(56) References Cited

U.S. PATENT DOCUMENTS

2009/0005703 A1    1/2009    Fasciano
2009/0131805 A1    5/2009    O'Brien et al.

OTHER PUBLICATIONS

Written Opinion of the International Searching Authority, issued in PCT/JP2015/057932 (PCT/ISA/237), dated Jun. 16, 2015.

Chinese Office Action dated Mar. 30, 2018 for corresponding Chinese Application No. 201580018232.2 (with English translation).

\* cited by examiner

DATA OUTPUT DEVICE AND METHOD, AND NON-TRANSITORY COMPUTER READABLE MEDIUM

CROSS-REFERENCE TO RELATED APPLICATION

This application is a Continuation of PCT International Application PCT/JP2015/057932 filed on 17 Mar. 2015, which claims priority under 35 U.S.C. 119(a) from Japanese Patent Application No. 2014-074276 filed on 31 Mar. 2014. The above application is hereby expressly incorporated by reference, in its entirety, into the present application.

BACKGROUND OF THE INVENTION

1. Field of the Invention

The present invention relates to a data output device and a data output method that output time-series data regarding medical care, and a non-transitory computer readable medium.

2. Description of the Related Art

In recent years, various medical care information acquired in medical care of a patient has been stored and managed as electronic data using a computer system. In the medical care information, for example, measured values of vital signs such as a heart rate, a pulse rate, blood pressure, and body temperature, inspection values in specimen inspection such as blood inspection, and data regarding treatment such as a name of an administered drug and a dosage are included. In medical care, it is important to recognize a transition of a condition of a patient such as a change over time in body temperature or blood pressure or a change in inspection values of a plurality of inspections performed in different periods of time, or recognize treatment or therapy in time series. Therefore, a display device that displays, in a graph form, time-series data in which measured values or an inspection values of a vital sign are recorded in time series is known (see, for example, JP2009-006147A (US2009/0005703A) and JP2011-500121A (US2009/0131805A)).

In JP2009-006147A (US2009/0005703A), a medical display device for monitoring and displaying inspection values such as those for intracranial pressure is described. In the medical display device of JP2009-006147A (US2009/0005703A), a current screen for displaying a graph of an inspection value measured most recently (for example, 10 to 15 seconds ago) from a current point in time, and a trend screen for displaying an average value of the inspection value in a graph in a relatively longer time scale than in the current screen are displayed. Since the trend screen has a longer time scale, it is easy to recognize a summary such as a trend of a transition of the inspection value, but it is difficult to recognize a detailed change in the inspection value. On the other hand, since the current screen has a shorter time scale, it is easy to recognize the detailed change in the inspection value, but it is difficult to recognize the summary of the transition of the inspection value. Further, in the trend screen, it is possible to assign an indicator indicating, for example, a timing at which a drug is administered, at a position designated on the graph.

Further, in JP2011-500121A (US2009/0131805A), a trend display for displaying, in a graph, a long-term change in an inspection value related to blood such as mean arterial pressure (MAP) and a sudden change display for enlarging and showing a sudden graph of an inspection value of a short period are simultaneously performed. Further, in JP2011-500121A (US Patent Publication US2009/0131805), it is possible to assign an indicator showing a timing at which a medical care action has been performed on the graph in the trend display.

In a case in which a screen that has a short time scale and displays details of the time-series data, like the trend screen and the current screen described in JP2009-006147A (US2009/0005703A) or the trend display and the sudden change display described in JP2011-500121A (US Patent Publication No. US2009/0131805), is a first display screen, and a screen that has a long time scale and displays a summary of the time-series data is a second display screen, an indicator is assigned in the second display screen in both of JP2009-006147A (US2009/0005703A) and JP2011-500121A (US2009/0131805A). However, since the second display screen is an area in which only the summary is displayed and the time scale is long, the indicator can only be assigned to a rough period. Therefore, for example, it is not possible to deal with a demand in a medical field for assignment of an indicator as a pinpoint to, for example, a sudden change point of the measurement value by referring to a daily change of a measurement value measured every day such as blood pressure.

Meanwhile, in a case in which the indicator is assigned to the first display screen, it is possible to cope with the above-described demand. However, there is a problem in that the risk of oversight of the indicator assigned in the past of the time-series data cannot be reduced only by the assignment of the indicator to the first display screen. This is because, although in the case of, for example, a patient visiting a hospital for a long period, time-series data is accumulated over a long period of time, all data of the time-series data cannot be displayed since a display range of the time-series data is limited in the first display screen having a shorter time scale than the second display screen. In an initial state, usually, a most recent part of the time-series data is displayed in the first display screen, and the display period displayed in the first display screen is changed over time. Therefore, an indicator assigned to a previous part of the time-series data is outside of a display range of the first display screen over time. A place that is noticed by a doctor and to which an indicator is attached in the medical field is likely to be very important. However, on the other hand, it is not realistic that a busy doctor remembers all places to which the indicators attached by the doctor. To recognize an entire image regarding medical care content of the patient and efficiently perform the medical care, a reduction in the risk of oversight of such important previous indicators is required. In the case of a patient visiting a hospital or hospitalized for a relatively long period of time, an acquisition period of time-series data is a long period. Accordingly, since the risk of the oversight correspondingly increases, such a case is particularly problematic.

SUMMARY OF THE INVENTION

An object of the present invention is to provide a data output device and a data output method capable of simply performing both of recognition of an entire image at an important point in time regarding medical care and recognition of a detailed change in time series data at the point in time, and a non-transitory computer readable medium.

In order to solve the above problem, a data output device of the present invention is a data output device for displaying time-series data indicating at least one of a transition of condition of a patient or content of medical care performed on the patient, and comprises a screen data generation unit, an indicator assignment instruction reception unit, and an indicator assignment unit. The screen data generation unit generates screen data of a data display screen including a first display area for displaying the time-series data, and a second display area for displaying a time axis in a time scale relatively longer than that of the first display area. The indicator assignment instruction reception unit receives an indicator assignment instruction to assign a first indicator to a designated position designated on the time-series data. The indicator assignment unit assigns the first indicator to the designated position in the first display area on the basis of the indicator assignment instruction, and assigns a second indicator indicating that there is the first indicator to a corresponding position that temporally corresponds to the designated position in the second display area.

It is preferable for the data output device to include a degree-of-importance setting unit that sets a degree of importance for at least one of the first indicator and the second indicator. This degree-of-importance setting unit changes a display mode of at least one of the first indicator or the second indicator according to the setting of the degree of importance.

It is preferable that, in the data display screen, in the event that one of the second indicators displayed in the second display area is selected, a first display period of the first display area is able to be changed to a display period including the first indicator corresponding to the selected second indicator.

It is preferable that, in the data display screen, a second display period of the second display area is able to be set according to a period in which there is the first indicator.

It is preferable that, in the data display screen, a period in which there is the first indicator is extracted from a most recent predetermined period, and the second display period is set.

It is preferable for the first indicator to be a tag in which text is able to be displayed.

It is preferable that the data display screen includes a list display area for displaying content of a plurality of first indicators as a list, in addition to the first display area and the second display area.

It is preferable that the first indicator is associated with an attribute of the time-series data to which the first indicator is assigned, and in the list display area, the first indicators to be displayed are narrowed down from among the plurality of first indicators according to the attribute.

It is preferable that only the first indicator displayed in the list display area is displayed in the first display area.

It is preferable that the time-series data includes at least one of data regarding a vital sign including at least one of a heart rate, a pulse rate, blood pressure, body temperature, or respiration, data regarding inspection, or data regarding treatment.

It is preferable that the data regarding the inspection includes an inspection value expressed as a numerical value, or an inspection image. It is preferable that the data on treatment includes administration content of a drug.

It is preferable that in the first display area, a plurality of pieces of time-series data is able to be displayed.

It is preferable that in the first display area, a display form of the time-series data is a graph or a table. Alternatively, both of the graph and the table may be displayed.

It is preferable that in the second display area, a data presence indicator indicating a data presence period in which there is time-series data is displayed along a time axis.

Further, a data output method of the present invention is a data output method for displaying time-series data indicating at least one of a state transition of a patient or content of medical care performed on the patient on a display unit, and comprises a screen data generation step, an indicator assignment instruction reception step, and an indicator assignment step. The screen data generation step includes generating screen data of a data display screen including a first display area for displaying the time-series data, and a second display area for displaying a time axis in a time scale relatively longer than that of the first display area. The indicator assignment instruction reception step includes receiving an indicator assignment instruction to assign a first indicator to a designated position designated on the time-series data. The indicator assignment step includes assigning the first indicator to the designated position in the first display area on the basis of the indicator assignment instruction, and assigning a second indicator indicating that there is the first indicator to a corresponding position that temporally corresponds to the designated position in the second display area.

A non-transitory computer readable medium according to the invention stores a computer-executable program enabling execution of computer instructions to perform operations for displaying time-series data indicating at least one of a state transition of a patient or content of medical care performed on the patient on a display unit. The operations include generating screen data of a data display screen including a first display area for displaying the time-series data, and a second display area for displaying a time axis in a time scale relatively longer than that of the first display area, receiving an indicator assignment instruction to assign a first indicator to a designated position designated on the time-series data, and assigning the first indicator to the designated position in the first display area on the basis of the indicator assignment instruction, and assigning a second indicator indicating that there is the first indicator to a corresponding position that temporally corresponds to the designated position in the second display area.

According to the present invention, it is possible to simply perform both of recognition of an entire image at an important point in time regarding medical care and recognition of a detailed change in time series data at the point in time.

BRIEF DESCRIPTION OF THE DRAWINGS

FIG. 5 is a block diagram illustrating an electrical configuration of a computer used for a data distribution server or the like.

DESCRIPTION OF THE PREFERRED EMBODIMENTS

[First Embodiment]

Figure 1:
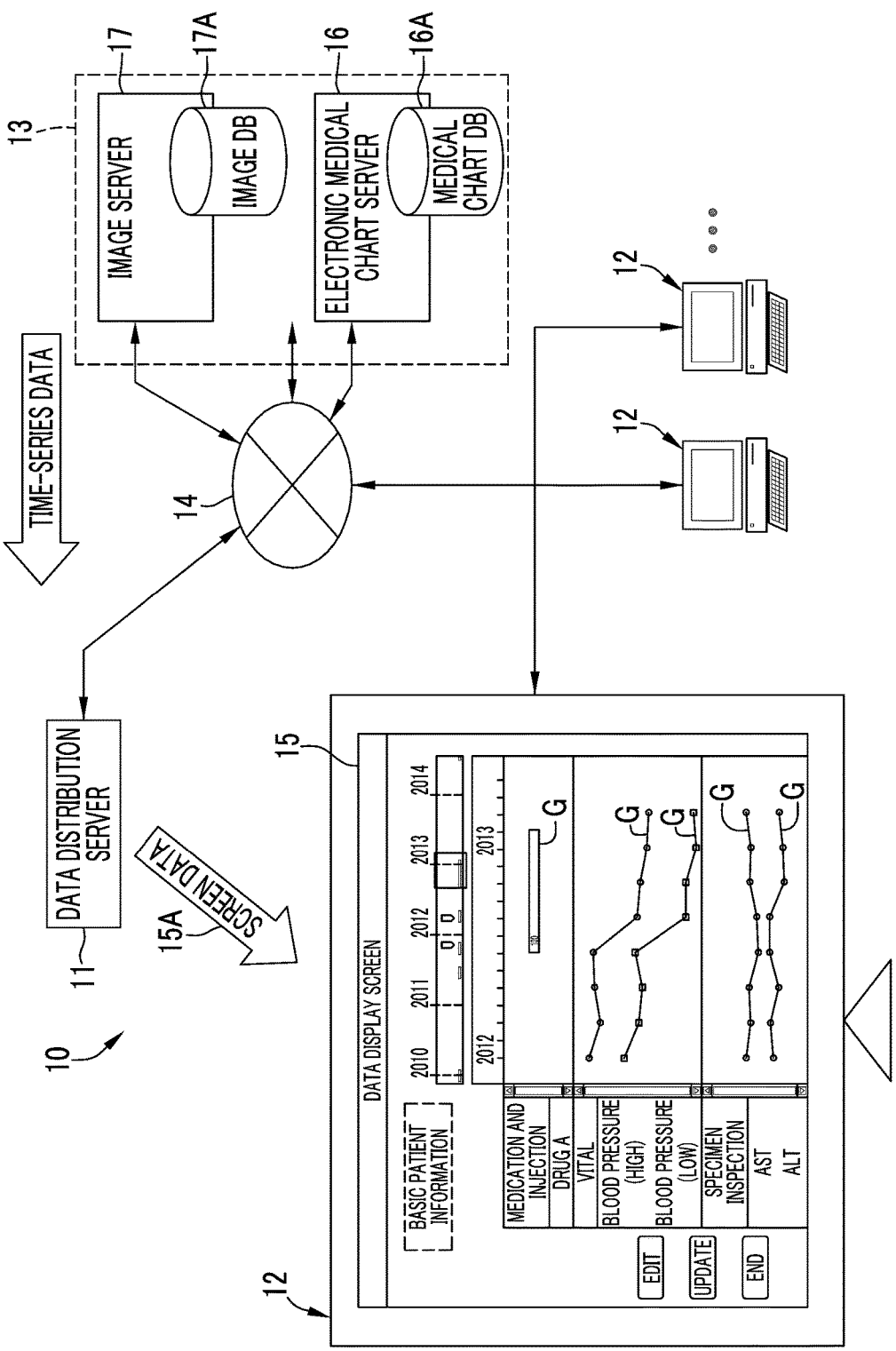
FIG. 1 is an illustrative diagram illustrating a configuration of a medical information system in which the present invention is embodied.

A medical information system 10 illustrated in FIG. 1 is a computer system that is used to manage information on medical care at a medical facility such as a hospital. This medical information system 10 includes a data distribution server 11, a client terminal 12, a server group 13, and a network 14 that connects the components so that the components can communicate with each other. In the server group 13, an electronic medical chart server 16, and an image server 17 are included. The network 14 is, for example, a local area network (LAN) that is laid in a hospital.

The client terminal 12 is a terminal that is installed in respective medical care departments such as an internal medicine, a surgery, an otolaryngology, and ophthalmology and is operated, for example, by a doctor in the medical care department. The client terminal 12 has a function of accessing the electronic medical chart server 16 and inputting and viewing electronic medical charts. Medical care information including a record of medical examination such as medical interview, inspection, or diagnosis, and a record of treatment such as treatment or surgery are input to the electronic medical chart. Further, the client terminal 12 has a function of accessing the image server 17 and viewing inspection images such as X-ray images.

Further, the client terminal 12 has a function of accessing the data distribution server 11 and viewing a data display screen 15 on which time-series data in which an inspection value or a measured value regarding a medical care of a patient is recorded in time series is displayed. In the data display screen 15, the time-series data is displayed, for example, in the form of a graph G. The client terminal 12 receives screen data 15A of the data display screen 15 from the data distribution server 11, and reproduces and displays the data display screen 15 on the basis of the screen data 15A.

The data distribution server 11 acquires the time-series data from the electronic medical chart server 16 or the image server 17 on the basis of a distribution request from the client terminal 12, generates the screen data 15A on the basis of the acquired time-series data, and distributes the generated screen data 15A to the client terminal 12 that is a request source. The data distribution server 11 is a data output device of the present invention that performs data distribution, which is one form of data output regarding the time-series data.

The electronic medical chart server 16 includes an electronic medical chart database 16A (hereinafter referred to as a medical chart DB) in which the electronic medical chart is stored. The image server 17 has an image DB 17A in which a plurality of inspection images are stored, and is a so-called Picture Archiving and Communication System (PACS) server. The chart DB 16A and the image DB 17A are databases in which search can be performed based on a keyword, such as a patient ID.

Figure 2:
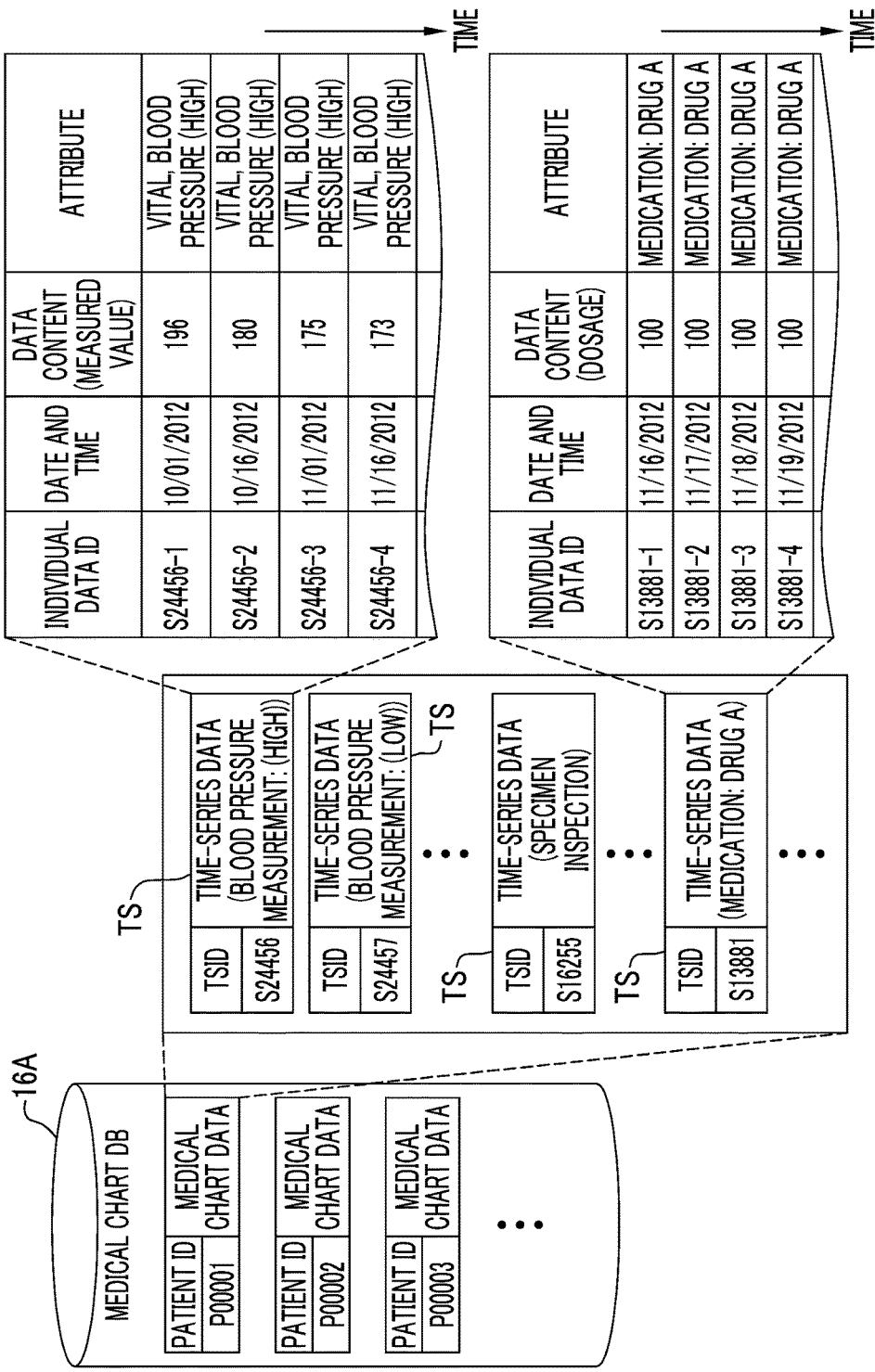
FIG. 2 is an illustrative diagram illustrating an example of time-series data recorded in an electronic medical chart.

As illustrated in FIG. 2, in the chart DB 16A, a patient ID (P00001, P00002 •••) is assigned to the medical chart data in which medical care information on the patient is recorded, and stored in units of patients. The medical chart data includes time-series data TS, in addition to basic patient information such as patient's name, date of birth, gender, and patient ID.

The time-series data TS is data indicating a state transition of a patient and content of medical care performed on the patient. The state transition of a patient refers to, for example, a temporal change in a measured value of a vital sign such as a heart rate, a pulse, blood pressure, body temperature, or respiration of a patient (data regarding the vital sign), or an inspection value of clinical inspection performed on a patient (data regarding inspection). The clinical inspection includes specimen inspection such as blood inspection or biochemical inspection, and physiological inspection such as electroencephalographic inspection. Time-series data indicating the state transition of the patient is a data series of a plurality of measured values or inspection values acquired over time. Content of medical care performed on the patient includes content of therapy such as medication, surgery, or treatment, or content of medical interview. Time-series data TS indicating the content of the medical care performed on the patient is time-series including data regarding medical interview or treatment, and indicating content of a plurality of medical cares performed over time. Administration content indicating a drug name or a dose of the drug is included in data of medication that is one of items of data regarding the treatment.

The time-series data TS is, typically, data series including a plurality of items of individual data acquired in time series for each of the same medical care items, such as blood pressure measurement and medication, as elements. As shown in this example, assuming that time-series data TS is time-series data TS of the blood pressure measurement, a plurality of measurement values for which measurement date are different constitutes a plurality of items of individual data as an element of the time-series data TS. From the time-series data TS of the blood pressure measurement, it is possible to confirm a change over time in the patient's blood pressure. In this example, the time-series data TS of the blood pressure measurement is divided into blood pressure (high) and blood pressure (low), which are recorded as one item of time-series data TS.

In the time-series data TS of medication, in a case in which the same drug is divided and administered in a plurality of times for a period of time, a dosage of each time constitutes a plurality of items of individual data as an element of the time-series data TS. Since the individual data of the medication in this example is recorded continuously for several days from 2012 Nov. 16 and the dosage of each individual data is the same amount ("100"), it can be confirmed from the time-series data TS of the medication that the same amount of a drug is administered to a patient once daily for several days.

A record of one piece of individual data includes, for example, data items: an individual data ID, date and time, data content (for example, measured value, dosage, or inspection data), and attribute. Information on the date and time is measurement date and time in the case of the measured value, inspection date and time in the case of the inspection value, and date and time in the event that medication has been performed or date and time of prescription in the case of the dosage. In a case in which the individual data is recorded a plurality of times a day, time information is also necessary so as to distinguish the respective items of individual data from one another, but in a case in which an acquisition frequency of the individual data is smaller than or equal to once per day, date information may be sufficient. The individual data ID is identification information that is assigned to each item of the individual data so as to specify the individual data. In this example, the individual data ID is provided as an independent data item separate from the date and time information, but since the individual data ID may specify the individual data, information on the date and time can be used as the individual data ID.

Further, since the medication may require a period until effects of the medication are expressed, for example, medication (taking a drug) over a predetermined period such as "taking drug by a predetermined amount in one day is continued for five days" may be instructed as one prescription. In this case, data of a prescription unit indicating content (a drug taking period and a dosage) of one prescription may be used as individual data. Date and time of this individual data is, for example, be prescription date and time.

The attribute is information assigned to classify data, and is information indicating a type of individual data. The attribute can also be used as a keyword for searching for the individual data. Further, since the individual data is an element of time-series data, the individual data has a meaning as information indicating a type of time-series data. Examples of the attribute include a name of the individual data, a category to which the individual data belongs, and a name of a medical care item regarding the individual data. In this example, as an attribute of individual data of blood pressure, a name of a measured value of "blood pressure (high)" is assigned, and a category "vital" is assigned since the blood pressure is one of vital signs. Further, since the measured value of the blood pressure is a numerical value, a type of data "numerical value data" can be assigned as an attribute or a category "measured value" distinguished from the "inspection value" can be assigned as an attribute. Further, a name "blood pressure measurement" of the medical care item can be assigned.

In the time-series data TS of medication, a name "medication" of the medical care item or a drug name "drug A" is assigned in the attribute. Further, as an attributes of medication, an administration method such as injection or taking may be assigned. The attribute may be automatically assigned according to content of input data by the electronic medical chart server 16, or may be assigned by manual input.

Further, content of medical interview is included in content of the medical care, in addition to content of treatment such as medication, but in the case of the medical interview, a medical interview record for each medical interview becomes individual data. A series of the individual data of the medical interview that is acquired in time series at different timings becomes time-series data of the medical interview.

IDs for identifying respective pieces of time-series data TS ("TSID") such as "S24456" and "S24457" are assigned to the respective pieces of time-series data TS. Therefore, using the patient IDs, the TSIDs, and the individual data IDs, the medical chart data, the time-series data TS within the medical chart data, and the individual data within the time-series data TS can be specified and searched for.

Figure 3:
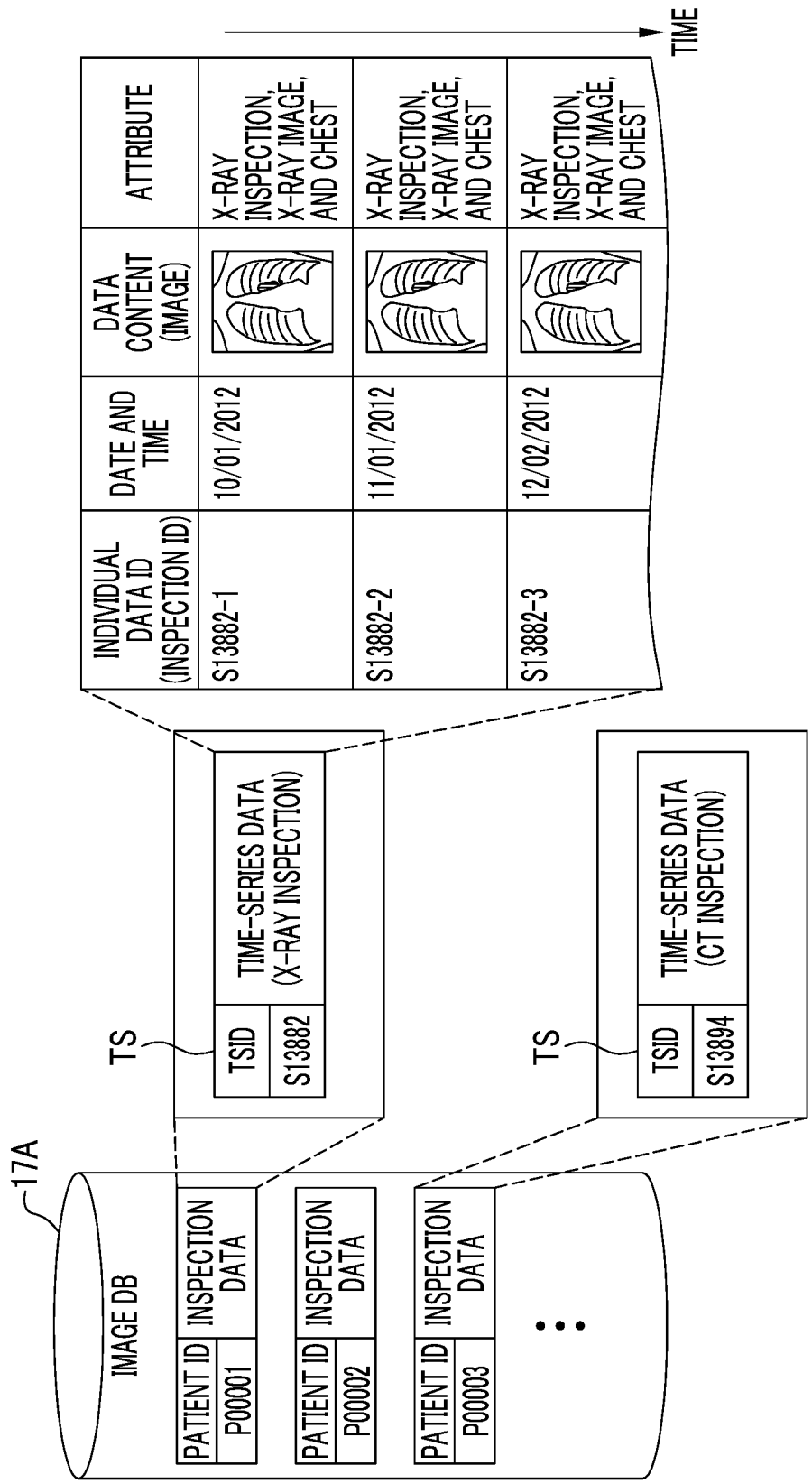
FIG. 3 is an illustrative diagram illustrating an example of time-series data recorded in an image server.

As illustrated in FIG. 3, inspection data including a plurality of inspection images captured in an image inspection such as an X-ray inspection or a CT inspection is stored in the image DB 17A. A patient ID is assigned to the inspection image, and the inspection image can be searched for using the patients ID. The image inspection may also be performed a plurality of times in medical care of one patient, as in a case in which progress observation is performed, and in this case, time-series data TS of the image inspection is acquired.

In the time-series data TS of the image inspection, the inspection image obtained by one image inspection becomes individual data. As an individual data ID, for example, an inspection ID is used. Since a plurality of tomographic images are acquired in one inspection in the case of the CT inspection, one piece of individual data includes a plurality of tomographic images. In the case of the X-ray inspection using a general X-ray imaging apparatus, since the number of X-ray images acquired in one inspection may be 1 or may be plural, the number of X-ray images in one piece of individual data may be 1 or may be plural. In an attribute of the individual data of the X-ray inspection, for example, information such as "X-ray inspection" indicating a type of inspection, "X-ray image" that is a type of image, and "chest" indicating an imaged part is assigned.

Figure 4:
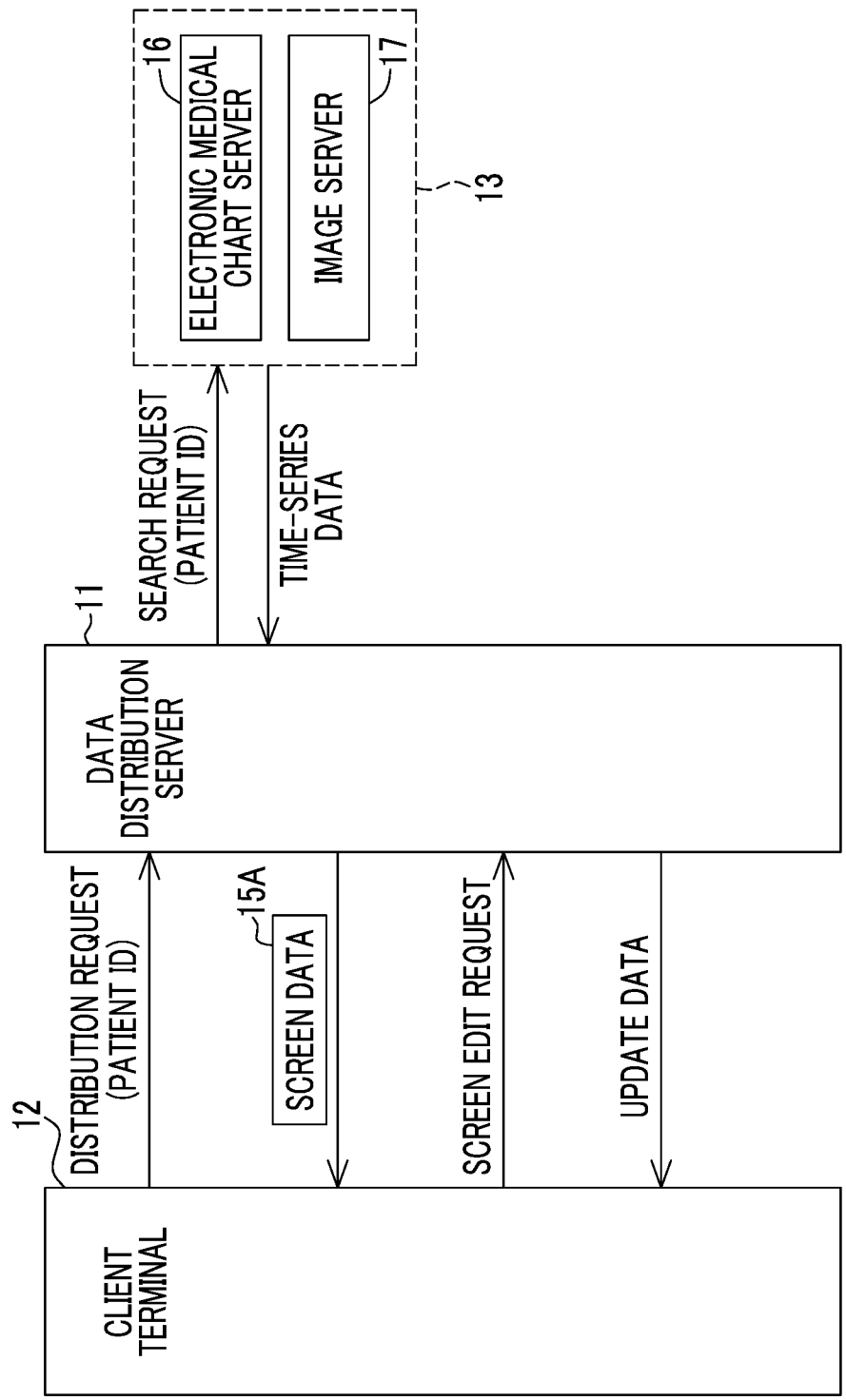
FIG. 4 is an illustrative diagram illustrating a flow of main information on the medical information system.

As illustrated in FIG. 4, the client terminal 12 receives the patient ID designated by an operation of a doctor, issues a distribution request including the designated patient ID, and transmits the distribution request to the data distribution server 11. Assuming that the data distribution server 11 receives the distribution request from the client terminal 12, the data distribution server 11 transmits a search request for time-series data TS to the electronic medical chart server 16 or the image server 17 using the patient ID as a search key. The electronic medical chart server 16 and the image server 17 search for each item of the time-series data TS regarding the patient ID from the chart DB 16A and the image DB 17A, and transmits the time-series data TS to the data distribution server 11. The data distribution server 11 generates the screen data 15A of the data display screen 15 on the basis of each item of the acquired time-series data TS, and distributes the screen data 15A to the client terminal 12 that is a request source for the distribution request.

The doctor views the data display screen 15 that is displayed on the client terminal 12. In the data display screen 15, screen editing such as changing a screen layout or changing a display item to be displayed in the data display screen 15, such as the time-series data TS to be displayed, can be performed through an editing operation of the doctor. Assuming that the client terminal 12 receives the editing operation, the client terminal 12 issues a screen edit request according to the editing operation and transmits the screen edit request to the data distribution server 11. Assuming that the data distribution server 11 receives the screen edit request, the data distribution server 11 performs an editing process according to content of the screen edit request to generate update data, and distributes the update data to the request source. The client terminal 12 updates the data display screen 15 on the basis of the update data.

The data distribution server 11, the client terminal 12, the electronic medical chart server 16, and the image server 17 are configured by installing a control program such as an operating system or an application program such as a client program or a server program in a computer such as a personal computer, a server computer, or a workstation.

Figure 5:
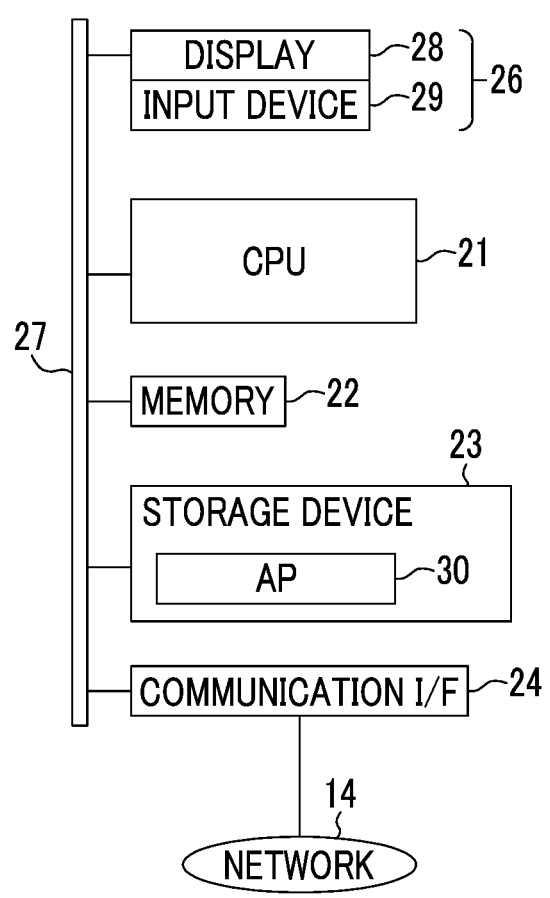

As illustrated in FIG. 5, a computer constituting each server 11, 16, or 17 or the client terminal 12 has the same basic configuration, and includes a central processing unit (CPU) 21, a memory 22, a storage device 23, a communication I/F 24, and an input and output unit 26. These are connected via a data bus 27. The input and output unit 26 includes a display (display unit) 28, and an input device 29 such as a keyboard or a mouse.

The storage device 23 is, for example, a hard disk drive (HDD), and a control program or an application program (hereinafter referred to as an AP) 30 is stored. Further, for example, a disk array in which a plurality of HDDs are connected and mounted is provided as a storage device 23 for a DB separately from the HDD that stores the program, in a server in which a DB is constructed. The disk array may be built into a main body of the server or may be provided separately from the main body of the server and connected to the main body of the server via a cable or a network.

The memory 22 is a work memory used for the CPU 21 to execute a process, and includes a random access memory (RAM). The CPU 21 loads a control program stored in the storage device 23 into the memory 22 and executes a process according to the program to control each unit of the computer. The communication I/F 24 is a network interface that performs transfer control with the network 14.

In the client terminal 12, a client program such as electronic medical chart software for performing viewing or editing of an electronic medical chart, or viewer software for performing viewing of inspection images or the data display screen 15 is installed as the AP 30. The viewer software may be, for example, dedicated software or may be a general-purpose WEB browser.

Figure 6:
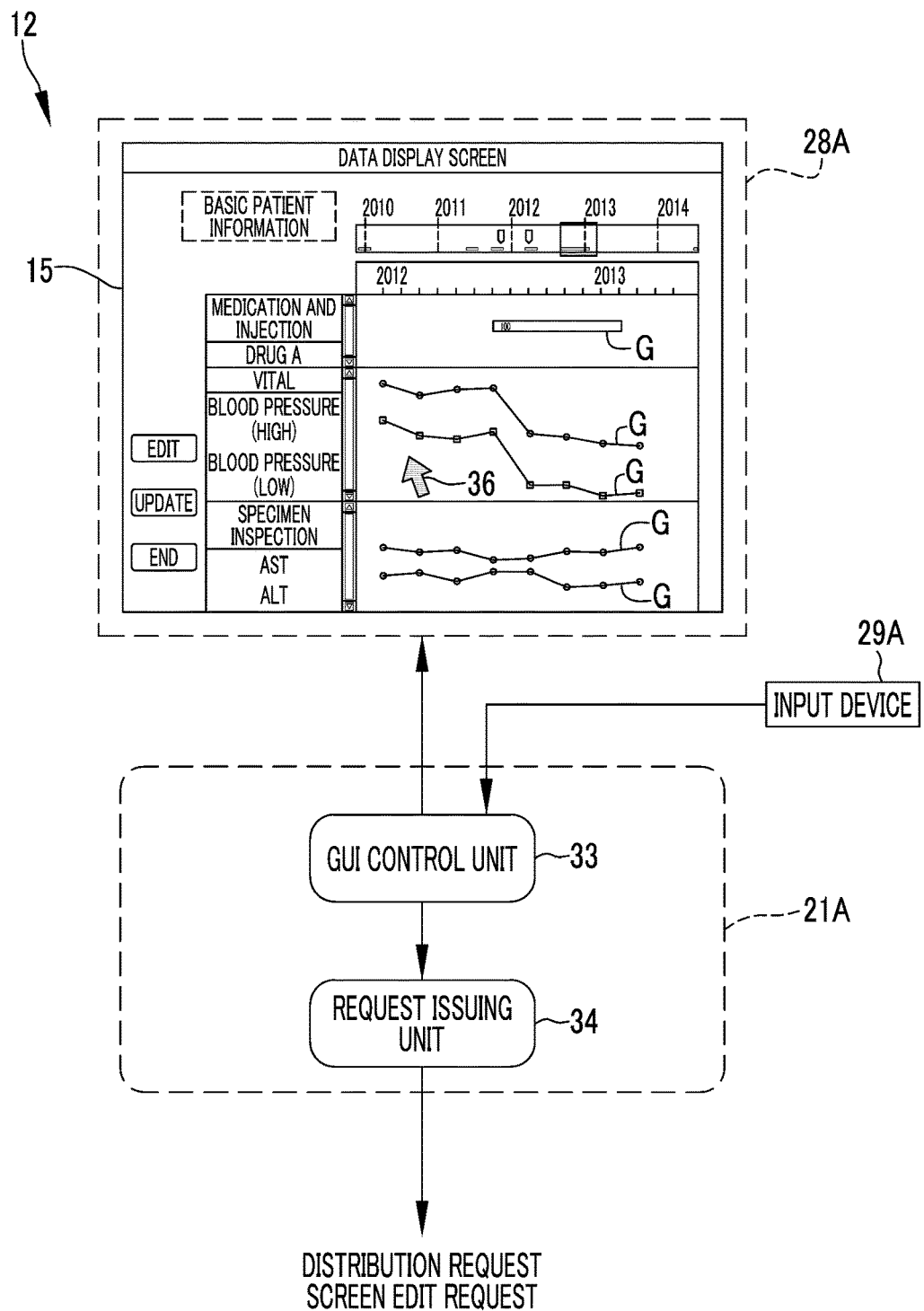
FIG. 6 is an illustrative diagram illustrating a functional overview of a client terminal.

As illustrated in FIG. 6, assuming that the viewer software for displaying the data display screen 15 starts up in the client terminal 12, a start-up screen having an operation function using a graphical user interface (GUI) is displayed on the display 28A of the client terminal 12. The CPU 21A of the client terminal 12 functions as a request issuing unit 34 that issues various requests for the GUI control unit 33 and the data distribution server 11 in cooperation with the memory 22. A designation of the patient ID in the start-up screen or an operation of issuing a distribution request for the screen data 15A of the data display screen 15 is performed.

The screen data 15A includes, for example, data described in a markup language such as Extensible Markup Language (XML), and the data display screen 15 that is reproduced by the screen data 15A also has an operation function using a GUI. The GUI control unit 33 reproduces the data display screen 15 on the basis of the screen data 15A and displays the data display screen 15 on the display 28A. Further, the GUI control unit 33 receives an operation instruction from the input device 29A through the data display screen 15 such as a click operation of an operation button using a pointer 36 of a mouse, and performs a screen control according to the received operation instruction. An instruction to issue the distribution request or the screen edit request is input to the request issuing unit 34 via the GUI control unit 33. The request issuing unit 34 issues a request to distribute the data display screen 15 of the designated patient ID and a screen edit request for the designated content according to the issuing instruction.

Figure 7:
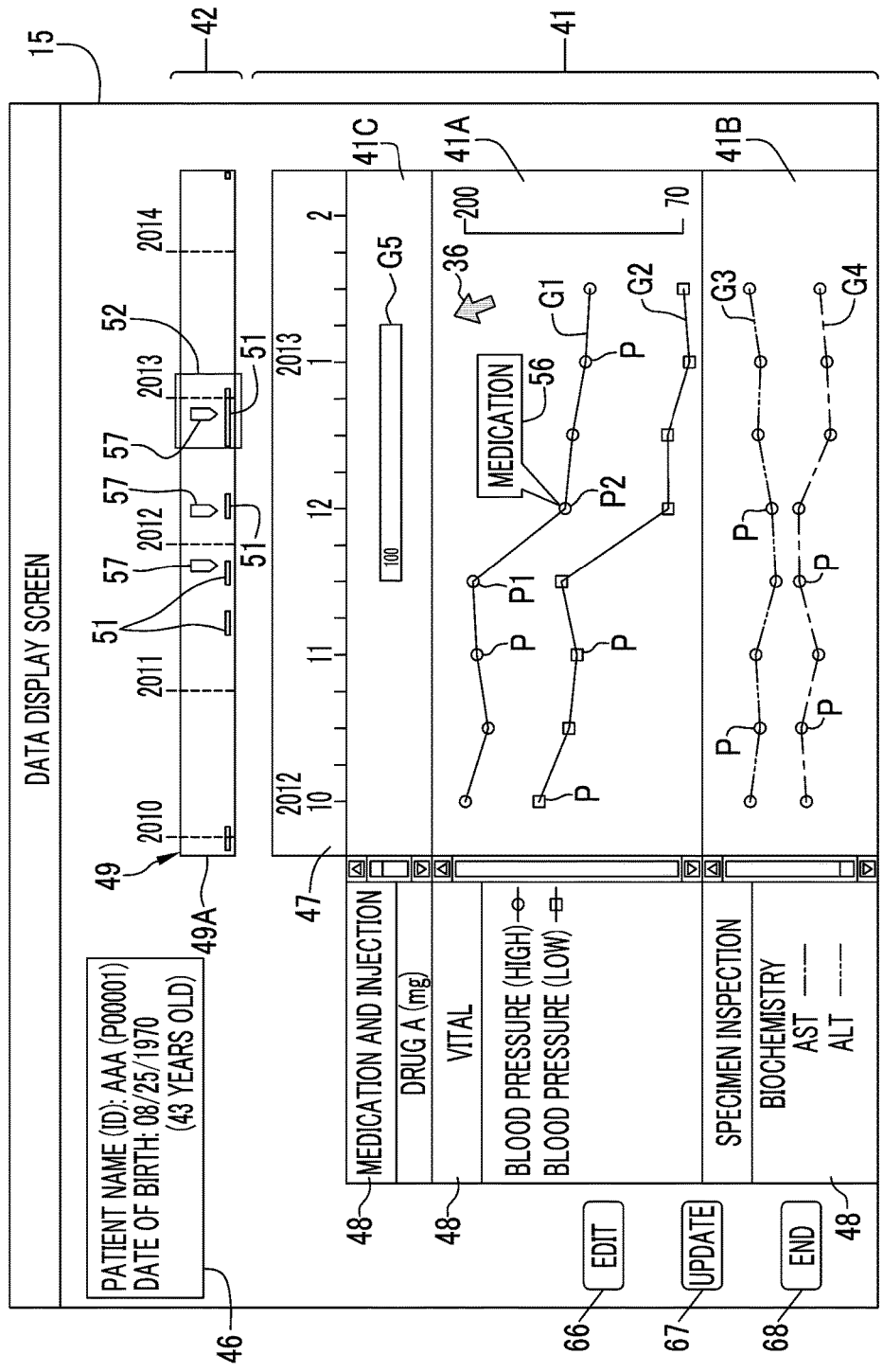
FIG. 7 is an illustrative diagram illustrating an example of a data display screen.

As illustrated in FIG. 7, the data display screen 15 includes a first display area 41, a second display area 42, and a basic information display area 46. Basic patient information, such as a patient name, patient ID, and age is displayed in the basic information display area 46.

The first display area 41 is a first display area for displaying the time-series data TS (graph G). In the first display area 41, a time is assigned to a horizontal axis. The first display area 41 is divided into a plurality of sub-areas 41A to 41C in a vertical direction. A first time axis 47 of the first display area 41 is provided in an upper portion of the first display area 41. In the first time axis 47, information such as year, month and day, and a scale are arranged according to a set time scale. The first time axis 47 has the same length as the first display period of the first display area 41, and also has a width in a vertical direction so that information can be displayed therein. In this example, the first display period is set to about four months from October 2012 to early February 2013. In the first time axis 47, a numeral indicating the year and the month of the four months, and a scale at a predetermined interval between the months are displayed.

In the first display area 41, data within the first display period in the time-series data TS is displayed in the form of a graph G. The first display period can be changed by a screen scroll operation in the horizontal direction. By this screen scroll operation, display of the year and the month of the first time axis 47 is changed, and a display range of the time-series data TS is changed. In the screen data 15A sent in one distribution from the data distribution server 11, time-series data TS of a longer period than the first display period is included. Therefore, the changing of the display range of the time-series data TS can be performed without redistribution from the data distribution server 11 so long as the range is a received range. In a case in which a change exceeding the received range is performed on the display range of the time-series data TS, additional distribution of the time-series data TS is received from the data distribution server 11.

A plurality of pieces of time-series data TS acquired in the first display period are displayed in the respective sub-areas 41A to 41C. Accordingly, a plurality of pieces of time-series data TS of the same period of time is comparably displayed. Five time-series data TS of different types is displayed in the form of graphs G1 to G5 in the respective sub-areas 41A to 41C. The type of time-series data TS to be displayed in the respective sub-areas 41A to 410 can be changed by a setting. A type and a name of the time-series data TS, and an item display field 48 for displaying medical care items regarding the time-series data TS are provided in each of the sub-areas 41A to 41C to the left of the respective sub-areas 41A to 41C.

In this example, the sub-area 41A of the second stage from the top, is set as an area for displaying the time-series data TS regarding vital signs such as blood pressure, body temperature, respiration, and a heart rate. More specifically, as the time-series data TS of the vital signs, the graphs G1 and G2 indicating a transition of measured values of the blood pressure are displayed. The graph G1 is a graph of blood pressure (high), and the graph G2 is a graph of blood pressure (low). The graphs G1 and G2 are line graphs that connect the input points P of a plurality of measured values (individual data) acquired in time series. Further, a scale of the measured value extending in a vertical direction (a lower limit "70" and an upper limit "200" in this example) is provided in a right end in the sub-area 41A. In the item display field 48 of the sub-area 41A, "vital" is displayed as a name of a large classification of the medical care item, and a name of a measured value indicated by the graphs G1 and G2 of "blood pressure (high)" and "blood pressure (low)" is displayed.

Further, since a plurality of graphs G1 and G2 are displayed within one area in the sub-area 41A, for example, different types of lines on which shapes of the input points P are distinguished by a square or a circle are assigned to the respective graphs G1 and G2 so as to identify the graphs G1 and G2. Line type information indicating whether the graphs G1 and G2 indicate high or low blood pressure is also displayed in the item display field 48 of the sub-area 41A. Although only the blood pressure is displayed as a vital sign in this example, body temperature, heart rate, or the like may be displayed in the sub-area 41A, in addition to the blood pressure. In this case, it is preferable for the line types and colors of the graphs to be changed so that each graph can be identified. It should be understood that only one graph G may be displayed in one sub-area instead of the plurality of graphs G being displayed in one sub-area.

The third stage of sub-area 41B is set as an area for displaying time-series data TS of an inspection value of specimen inspection, and graphs G3 and G4 indicating a transition of the inspection value are displayed. The graphs G3 and G4 are, for example, inspection values of biochemistry inspection, which is one of specimen inspections, the graph G3 is an inspection value of AST (aspartate aminotransferase), and the graph G4 is an inspection value of ALT (alanine aminotransferase). The graphs G3 and G4 are line graphs that connect the input points P of a plurality of inspection values (individual data) acquired in times series, similar to the graphs G1 and G2. "Specimen inspection" as a name of a large classification of the medical care item, "biochemistry" as a name of a middle classification of the medical care item, and "AST" and "ALT" as a name of the inspection value indicated by the graphs G3 and G4 are displayed in the item display field 48 of the sub-area 41B. Further, line type information for identifying the graphs G3 and G4 are also displayed.

The first stage of the sub-area 41C is set as an area for displaying the time-series data TS of drug administration, such as medication or injection, and a graph G5 indicating a period in which drug administration has been performed is displayed. In this example, since the dosage is constant over an entire period, the graph G5 is displayed in the form of a bar graph extending straight in a horizontal direction. Assuming that the dosage is changed, the graph G5 is changed in the vertical direction. A display indicating a numerical value ("100") of dosage is inserted into the graph G5. "Medication and injection" as a name of a large classification of the medical care item, "Drug A" as a drug name, "mg" as a unit of dosage, and the like are displayed in an item display field 48 of the sub-area 41C. In this example, only a graph of one type of drug is displayed, but a graph of a plurality of drugs can be displayed.

Further, although not illustrated, a plurality of thumbnail images are arranged along the time axis in a case in which the time-series data TS of the image inspection is displayed in the sub-area. Although the example in which the first display area 41 is divided into three sub-areas has been described in this example, the number of divisions is not limited to three, but may be two or may be three or greater. In a case in which there are the number of sub-areas equal to or greater than the number of sub-areas that can be simultaneously displayed in the first display area 41, a hidden sub-area may be able to be displayed by, for example, the screen scroll operation in the vertical direction. Further, it should be understood that the first display area 41 may not be divided.

The second display area 42 has a relatively longer time scale than the first display area 41, and a second time axis 49 of which the time scale is longer than the first time axis 47 is displayed in the second display area 42. The second time axis 49 has a display frame 49A having a width in a vertical direction in which information can be displayed therein, similar to the first time axis 47. In the second time axis 49, a numeral such as year, month, and day is displayed in an upper portion of the display frame 49A. A scale is displayed in each year inside the display frame 49A. The numeral of year, month and day, and the scale are arranged according to a set time scale.

A length of the second time axis 49 corresponds to a length of the second display period of the second display area 42. The second display period has a longer time scale than the first display period of the first display area 41, and the first display area 41 and the second display area 42 in the data display screen 15 have substantially the same widths. Therefore, for a period of a part in the second time axis 49, detailed display can be performed in the first display area 41.

In FIG. 7, time-series data TS (graph G) in a part of the second display period is displayed in the first display area 41. In this example, the first display period is set to about four months from October 2012 to early February 2013, and the second display period is set to about four and a half years from 2010 to a first half of 2014 including the first display period of four months. The first display period and the second display period can be changed by a setting.

A data presence indicator 51 indicating that there is the time-series data TS in the second display period is displayed within the display frame 49A of the second time axis 49. Since the presence of the time-series data TS indicates that any medical care has been performed, the data presence indicator 51 also functions as an indicator indicating a day or a period in which the medical care has been performed. Thus, the data presence indicator 51 indicates a data presence period. The data presence indicator 51 is, for example, a bar-shaped indicator extending in the direction of the second time axis 49. Further, a period indicator 52 is displayed in the display frame 49A.

Figure 8:
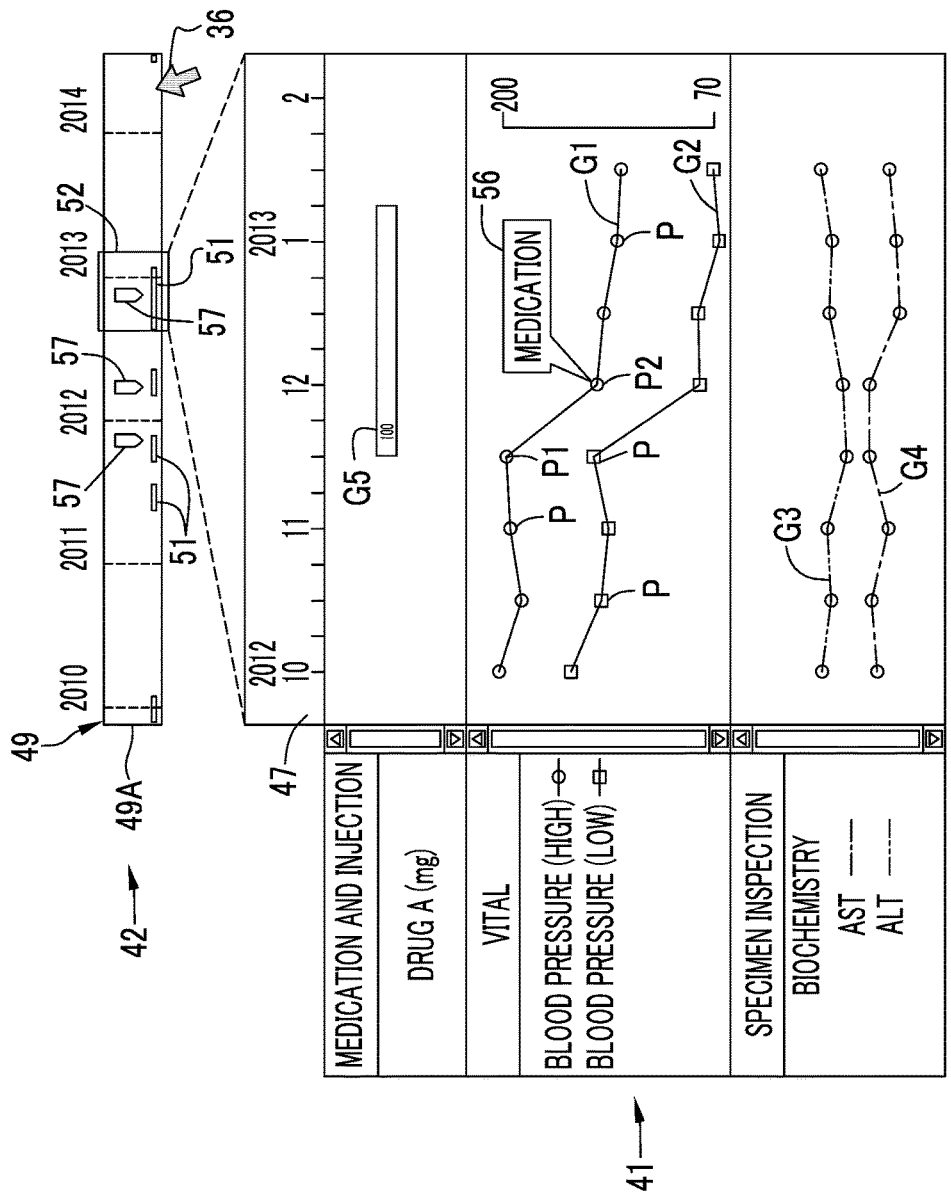
FIG. 8 is an illustrative diagram illustrating a relationship between a period indicator and a first display period of a first display area.

As illustrated in FIG. 8, the period indicator 52 is an indicator indicating a range in which the first display period of the first display area 41 is on the second time axis 49. A width of the period indicator 52 corresponds to a length of the first display period in the time scale of the second time axis 49. In this example, since the first display period is about four months, the width of the period indicator 52 is a width of about four months in the time scale of the second time axis 49. Further, the period indicator 52 also functions as an operation portion for changing the first display period of the first display area 41. The period indicator 52 has an operation portion slidable on the second time axis 49. Assuming that the period indicator 52 is designated by the pointer 36 and a slide operation is performed, the first display period of the first display area 41 is also changed. For example, assuming that the period indicator 52 is moved from a position of 2013 to a position of 2012 in the second time axis 49 by the slide operation, the first display period displayed in the first display area 41 is changed from 2013 to 2012.

Since the data presence indicator 51 is displayed in the second time axis 49, the time-series data TS of a movement destination can be displayed in the first display area 41 assuming that the period indicator 52 is moved to a position of the data presence indicator 51.

Further, in the data display screen 15, a first indicator 56 can be assigned at a designated position designated in the time-series data TS displayed in the first display area 41. In the case of the graphs G1 to G4, at least any one of a plurality of input points P of individual data may be designated as the designated position. In the case of the graph G5, at least any one of points on the graph G5 may be designated. In the case of the graph G5 of medication, continuous medication is performed in a predetermined period. In the case of the medication, since a predetermined period is defined as a period required to express a medication effect, the entire medication period may have a meaning as one treatment. Therefore, in the case of the medication of the graph G5, the entire medication period (entire graph G5) may also be designated as the designated position.

Assuming that the first indicator 56 is assigned, a second indicator 57 is assigned at a corresponding position that temporally corresponds to the first indicator 56 in the second display area 42. The corresponding position that corresponds in time is a position in the second display area 42 which is the same date and time as the date and time at which the first indicator is assigned. The second indicator 57 is an indicator indicating a position in the second time axis 49 at which there is the first indicator 56. The second indicator 57 is displayed within the display frame 49A together with the data presence indicator 51. In the second time axis 49, the second indicator 57 is not only displayed in the period indicated by the period indicator 52, but also displayed at a position outside the first display period. In this example, the first display period is a period from October 2012 to early February 2013 and the period indicator 52 also indicates that period, but in the second time axis 49, the second indicator 57 is also displayed at a position corresponding to the outside of the first display period such as 2011 or a first half of 2012. Therefore, it is possible to confirm the presence of the first indicator 56 and an approximate period of time in which there is the first indicator 56 in the first display period displayed in the first display area 41, as well as in the outside of the first display period.

The first indicator 56 is assigned at a position determined to be important by the doctor in the time-series data TS. For example, it can be seen from the graph G1 that a blood pressure transitions to a relatively high state before an input point P1, suddenly decreases between input points P1 and P2, and is stabilized at a relatively low state after P2. For example, the doctor determines that the input point P2 is an important change point of the blood pressure, designates the input point P2, and assigns the first indicator 56.

Further, in the first indicator 56 is, for example, a comment can be input as a text, and the first indicator 56 includes an object in a tag form in which the input comment can be displayed. A period of time in which the blood pressure decreases between the input points P1 and P2 overlaps a period of time in which the medication starts, as shown in the graph G5. In such a case, a causal relationship between the medication and the decrease in blood pressure, such as an effect of the decrease in blood pressure due to a cause of medication, can be confirmed. For example, in a case in which the doctor has made such a determination, a comment indicating the causal relationship can be input to the first indicator 56. In the case of this example, a comment indicating the cause "medication" is input to the first indicator 56 assigned to the input point P2 indicating the effect of reduction in the blood pressure.

Thus, the first indicator 56 is assigned at the position determined to be important by the doctor in the time-series data TS. In the second display area 42, the second indicator 57 is assigned at a corresponding position that corresponds to the first indicator 56. Since the second display area 42 has a longer time scale than the first display area 41, the assignment of the second indicator 57 in the second display area 42 makes it possible to easily confirm, for example, the presence of the first indicator 56 assigned in the past although the first indicator 56 is not displayed in the first display area 41 that is currently displayed. In a case in which the patient visits a hospital or is hospitalized for a long period of time, a plurality of first indicators 56 may be assigned. Accordingly, the second indicators 57 corresponding to the first indicators 56 can be easily confirmed in the second display area 42 and it is possible to prevent oversight and improve efficiency of diagnosis.

Further, in the data display screen 15, assuming that any one of the second indicators 57 in the second display area 42 is selected, the first display period of the first display area 41 is changed to a display period including the first indicator 56 corresponding to the selected second indicator 57. As described above, the first display period of the first display area 41 can also be changed by an operation of the period indicator 52 or can be changed by a selection operation of the second indicator 57.

Figure 9:
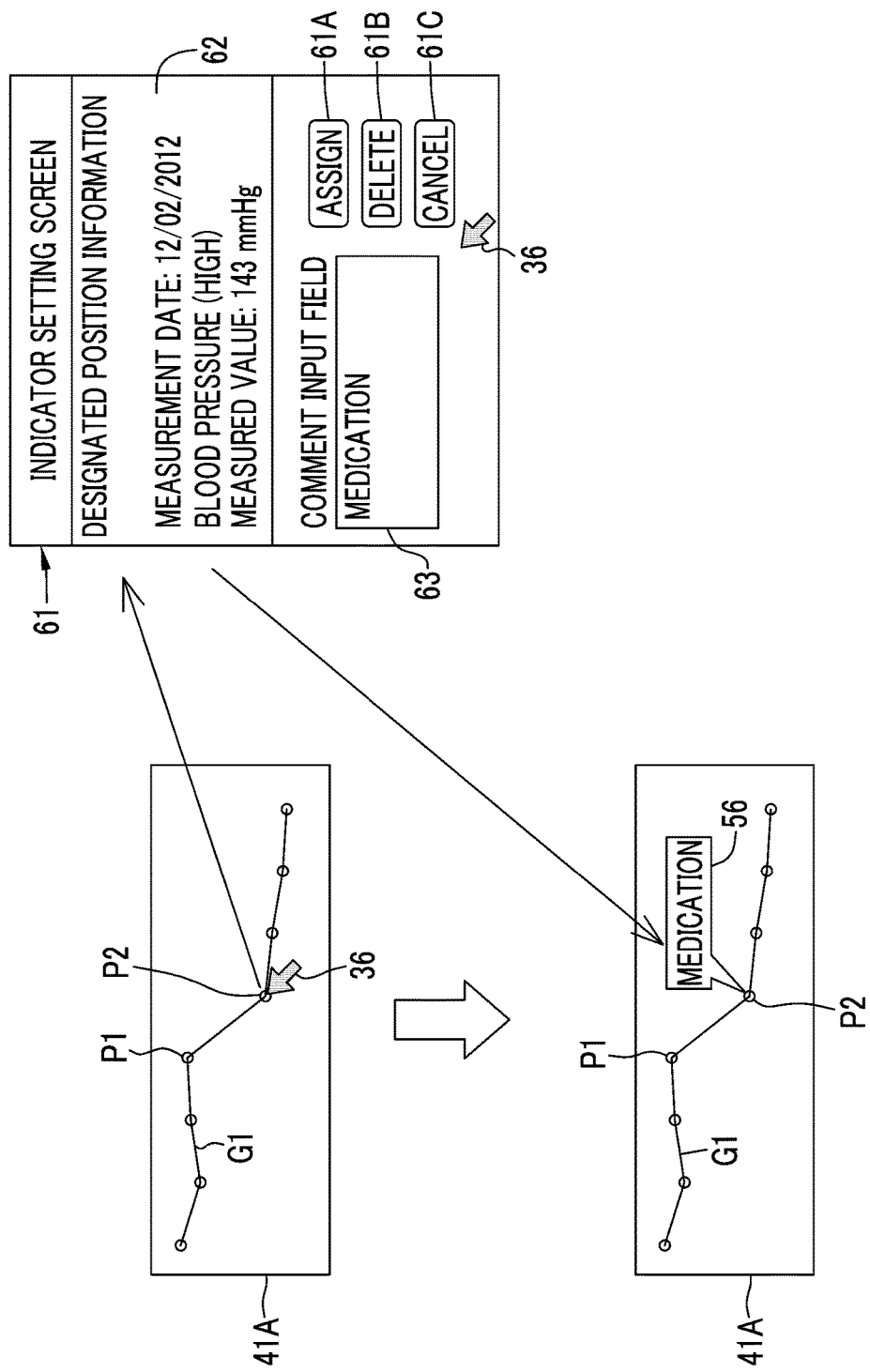
FIG. 9 is an illustrative diagram illustrating a procedure of assigning a first indicator.

An assignment operation of the first indicator 56 is performed, for example, in the following procedure. First, an arbitrary position on the graph G is designated by the pointer 36 and a click operation is performed. Assuming that the click operation is performed, an indicator setting screen 61 illustrated in FIG. 9 is opened on the data display screen 15. In the indicator setting screen 61, a display field 62 in which designated position information on the designated position is displayed, a comment input field 63, an assignment button 61A, a deletion button 61B, and a cancel button 61C are provided. In the display field 62, information on individual data of the designated position is displayed. Since the individual data of the input point P2 is a measured value of the blood pressure (high) assuming that the input point P2 is the designated position, for example, a name ("blood pressure (high)") of the measured value, measurement date ("2012/12/02"), and a measured value ("143") are displayed in the display field 62.

A comment input field 63 is an input field for inputting a comment such as "medication" to the first indicator 56 in a tag form. The assignment button 61A is an operation button for inputting an indicator assignment instruction. Assuming that the assignment button 61A is operated, the first indicator 56 of the content set in the indicator setting screen is assigned. In the event that the first indicator 56 is assigned, the second indicator 57 is automatically assigned to the corresponding position of the first indicator 56.

The deletion button 61B is an operation button for deleting the first indicator 56 that has been once assigned. For example, in the event that the input point P2 is clicked on with the pointer 36 even in a case in which the first indicator 56 has been assigned to the input point P2, the indicator setting screen 61 is opened. In the event that the deletion button 61B is operated at this time, the assigned first indicator 56 is deleted. A cancel button 61C is an operation button for canceling operation content in a state in which the indicator setting screen 61 is opened. Assuming that the cancel button 61C is operated, return to a state before the indicator setting screen 61 is opened occurs.

In the event that such an assignment operation of the first indicator 56 is performed, the request issuing unit 34 issues a screen edit request including an indicator assignment instruction of the first indicator 56. The screen edit request is transmitted to the data distribution server 11.

In FIG. 7, an edit button 66, an update button 67, and an end button 68 are provided to the left of the first display area 41 on the data display screen 15. The edit button 66 is an operation button for performing editing of the data display screen 15. Assuming that the edit button 66 is operated, for example, an edit menu screen (not illustrated) for instructing the screen editing pops up. Screen editing items include, for example, setting of a display period or a time scale of the first display area 41 and the second display area 42, and setting of the number of divisions of sub-areas of the first display area 41. Further, there is a setting of display items such as the time-series data TS displayed in each sub-area or information displayed in areas other than the item display field 48. A screen layout may be changed. For example, the display positions of the first display area 41 and the second display area 42 are reversed. Further, an item for assigning the first indicator 56 may be displayed in the edit menu screen. Assuming that the screen editing is instructed by the editing menu screen, the request issuing unit 34 issues a screen edit request according to designated content, and the screen edit request is transmitted to the data distribution server 11.

The update button 67 is an operation button for updating the data display screen 15. In a case in which any screen editing instruction is input at the point in time at which the update button 67 is operated, the request issuing unit 34 issues a screen edit request including the input screen editing instruction assuming that the update button 67 is operated. Assuming that there is no screen edit instruction, the request issuing unit 34 issues a distribution request to reload the screen data 15A of the data display screen 15 in an editing state at that point in time. The end button 68 is an operation button for ending the data display screen 15.

Figure 10:
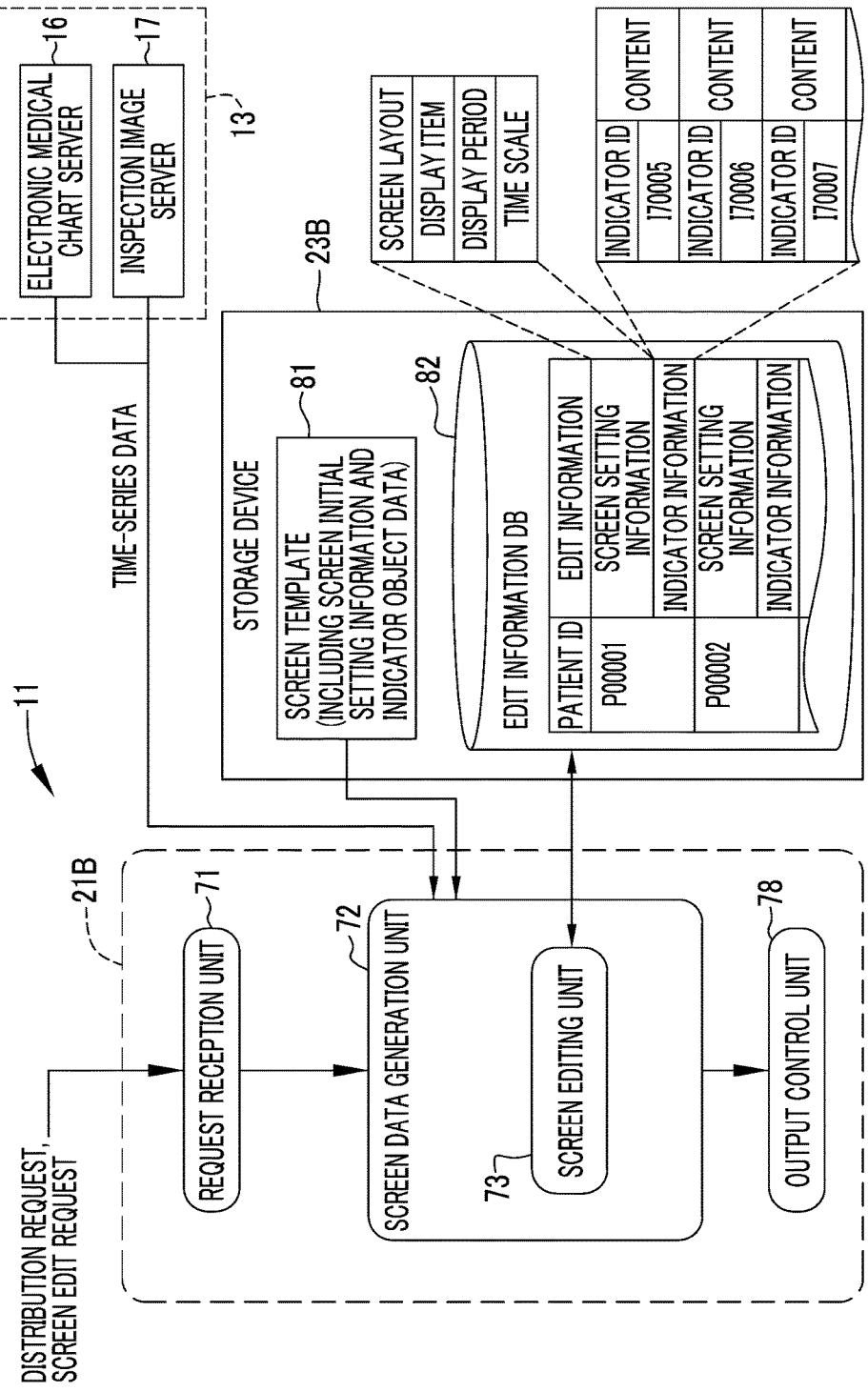
FIG. 10 is an illustrative diagram illustrating a schematic function of a data distribution server.

As illustrated in FIG. 10, a data distribution server program is installed as an AP 30 in the data distribution server 11. Assuming that the program is executed, the CPU 21B of the data distribution server 11 functions as a request reception unit 71, a screen data generation unit 72, and an output control unit 78 in cooperation with the memory 22. The request reception unit 71 receives various requests from the client terminal 12. In a case in which the request reception unit 71 receives a distribution request or a screen edit request, the request reception unit 71 inputs the received request to the screen data generation unit 72. The request reception unit 71 also receives the screen edit request including an indicator assignment instruction for the first indicator 56. Accordingly, the request reception unit 71 is an indicator assignment instruction reception unit that receives an indicator assignment instruction for assigning the first indicator at the specified designated position in the time-series data.

The screen data generation unit 72 generates the screen data 15A of the data display screen 15 for displaying the time-series data TS regarding the patient ID designated in the distribution request on the basis of the input distribution request. The screen data 15A is XML data for WEB distribution, as described above. In the event that the screen data generation unit 72 generates the screen data 15A, the screen data generation unit 72 uses a screen template 81 and an edit information DB 82 stored in the storage device 23B of the data distribution server 11. A screen editing unit 73 is provided in the screen data generation unit 72. The screen editing unit 73 edits the screen data 15A on the basis of the edit information.

The screen template 81 includes data such as an initial screen setting information on the data display screen 15 or indicator object data. The initial screen information is initial setting information, such as a display period or a time scale of each of the first display area 41 and the second display area 42, the number of divisions of the first display area 41, and a screen layout in the data display screen 15. The indicator object data is object data such as icons inserted into the data display screen 15, such as the first indicator 56 and the second indicator 57.

The edit information DB 82 is a database that stores edit information in a case in which a user has edited the data display screen 15. In the data display screen 15, since the time-series data TS is displayed in units of patients, the edit information is also stored for each patient ID. The edit information includes the screen setting information on the screen layout, display items, the display period, and the time scale, and indicator information on the first indicator 56 and the second indicator 57. The indicator information is information such as the designated position of the first indicator 56. In a case in which a plurality of first indicators 56 are assigned, a plurality indicator information is stored. Each indicator information is data such as the designated position indicator, and an ID is assigned to each pieces of indicator information.

The screen data generation unit 72 reads the edit information on the designated patient ID from the edit information DB 82 on the basis of the distribution request. The screen data generation unit 72 checks the display items such as the time-series data TS displayed on the data display screen 15 on the basis of the screen setting information on the edit information, and acquires the time-series data TS from the server group 13.

In a case in which there is the edit information on the designated patient ID, the screen editing unit 73 processes the screen template 81 to perform a screen editing on the basis of the edit information. For example, the screen editing unit 73 converts the acquired time-series data TS into a graph display form according to the display period or the time scale of the first display area 41 within the edit information. The graph after conversion is inserted into the screen template 81. Further, in a case in which there is, for example, a designation of the screen layout in the edit information, the designated screen editing is performed to generate the screen data 15A. Further, individual data of a part within the display range of the time-series data TS and at least a part including a part before and after such a part is added to the screen data 15A. In a case in which the time-series data TS is an image, for example, a thumbnail image is added.

Further, in a case in which the screen edit request is received after the screen data 15A is distributed, the screen editing unit 73 performs screen editing according to the screen edit request and generates update data. The update data, for example, may be the entire updated screen data 15A or may be a part required for update. Further, the screen editing unit 73 updates the edit information in the edit information DB 82 with content of the received screen edit request.

Figure 11:
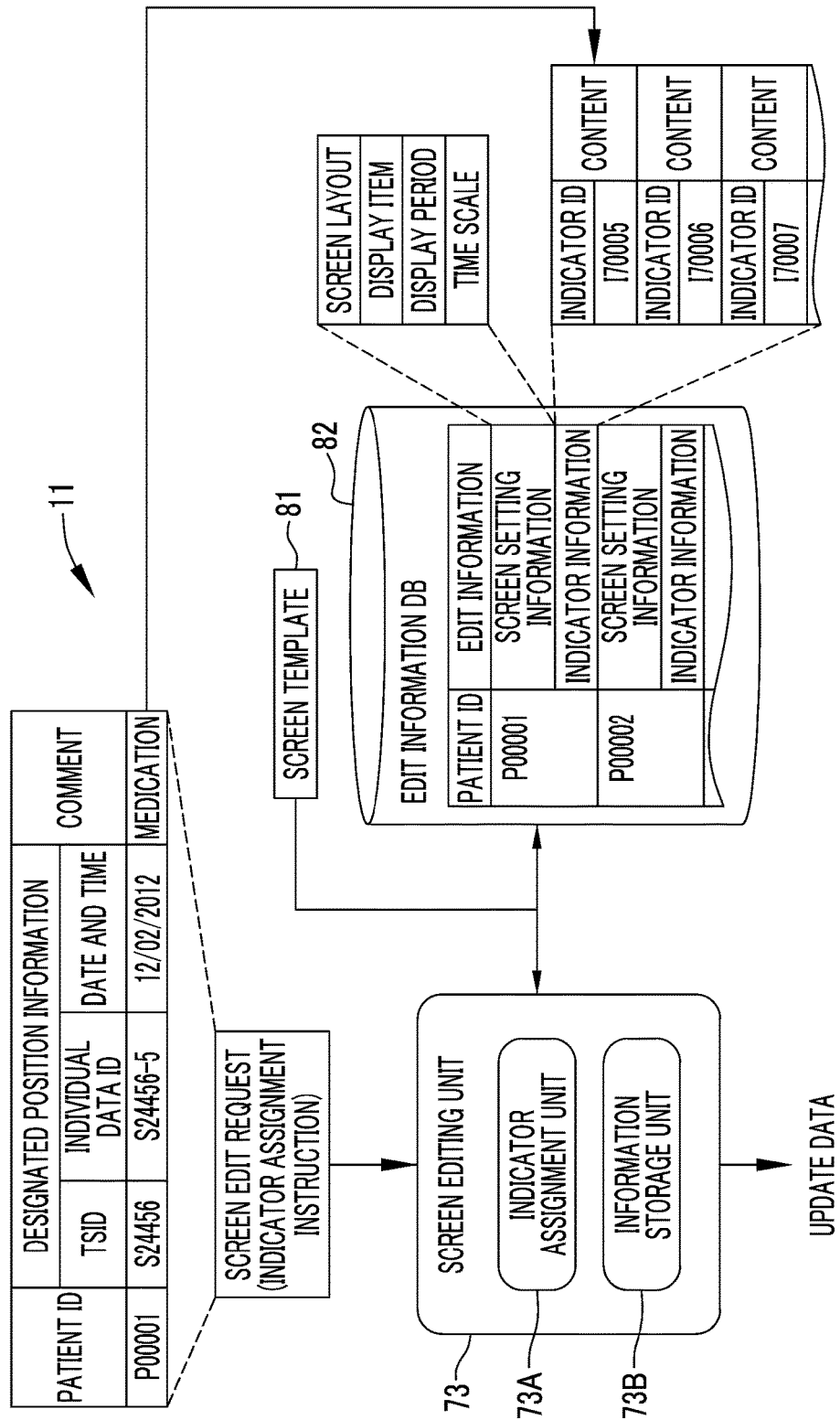
FIG. 11 is an illustrative diagram illustrating a schematic function of a screen editing unit regarding indicator assignment.

As illustrated in FIG. 11, an indicator assignment unit 73A that performs an indicator assignment process, and an information storage unit 73B are provided in the screen editing unit 73. In a case in which there is an indicator assignment instruction in the screen edit request newly received by the request reception unit 71 or in a case in which the indicator information has been already stored in the edit information, the indicator assignment unit 73A assigns the first indicator 56 and the second indicator 57 as one screen editing on the basis of the indicator assignment instruction or the indicator information. The information storage unit 733 stores content of the screen edit request including the indicator assignment instruction as edit information in the edit information DB 82. In the case of the indicator assignment instruction, content of the indicator assignment instruction is stored as the indicator information.

In the indicator assignment instruction, a patient ID, an TSID of the time-series data TS, an individual data ID, time and date information, and information on an input comment are included according to content set in the indicator setting screen 61. The indicator assignment unit 73A reads the designated position from the newly received indicator assignment instruction or the indicator information within the edit information DB 82, specifies the designated position in the time-series data TS (graph G) designated within the data display screen 15, and assigns the first indicator 56 at the specified designated position. The indicator assignment unit 73A specifies the display position corresponding to the same date and time within the second display area 42 according to the specified designated position and the time scale of the first display area 41 and the second display area 42, and assigns the second indicator 57 at the designated display position.

In FIG. 10, meanwhile, in a case in which screen data 15A of a new patient ID is generated, the screen data generation unit 72 generates the screen data 15A as an initial setting according to the screen template 81. In this case, the time-series data TS to be displayed may be determined, for example, with initial screen setting information, like a display of "blood pressure" and "body temperature" for the vital, and selection of the time-series data TS may be inquired of the client terminal 12. In this case, the screen data generation unit 72 waits for the selection information for the time-series data TS from the client terminal 12, receives the selection information, acquires the time-series data TS from the server group 13, and then generates the screen data 15A.

The output control unit 78 performs control to distribute the screen data 15A generated by the screen data generation unit 72 or the update data to the client terminal 12 that is a request source. The client terminal 12 displays the data display screen 15 on the display 28A on the basis of the received screen data 15A or update data.

Figure 12:
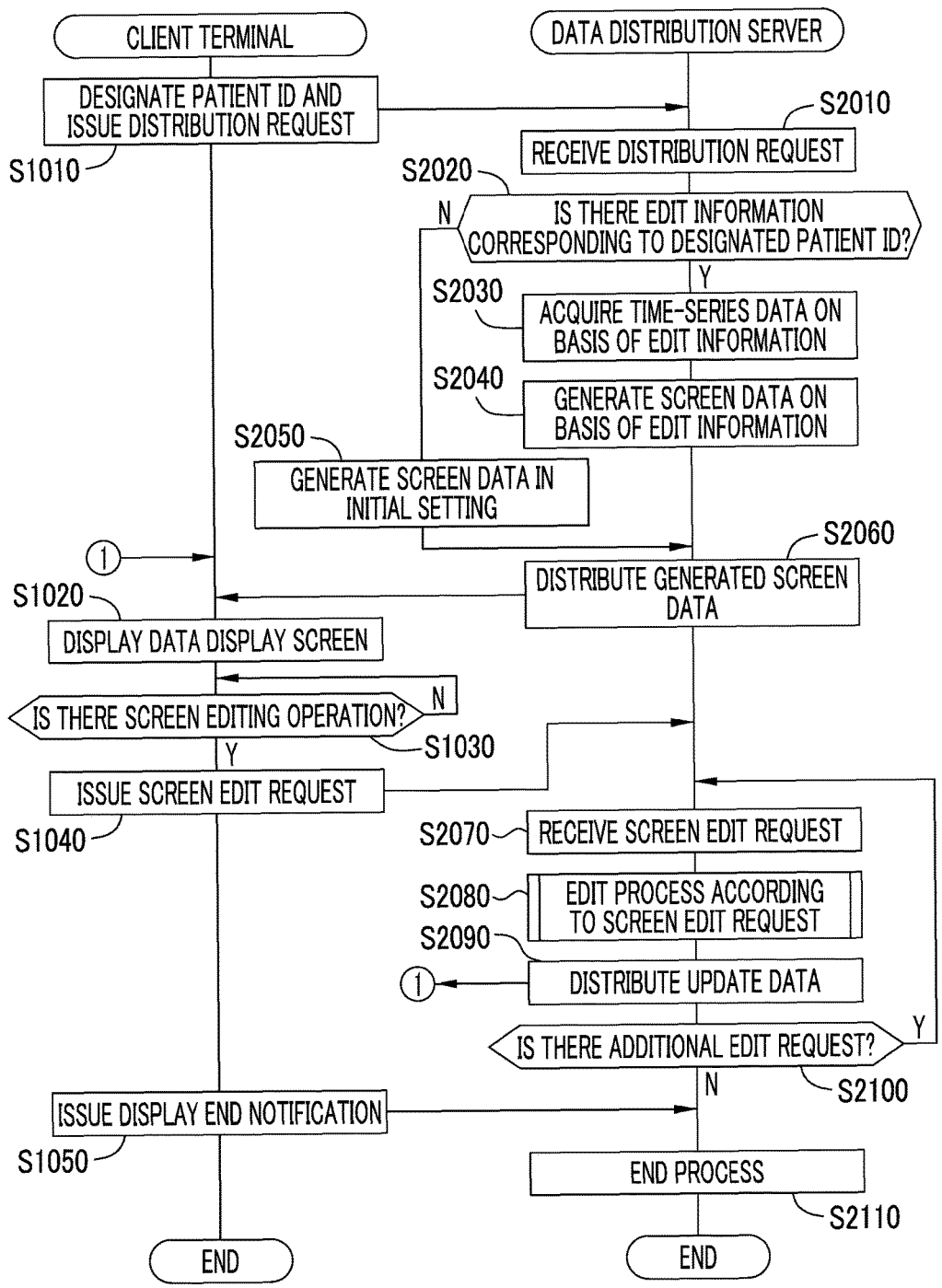
FIG. 12 is a flowchart illustrating a schematic procedure of a display and editing of a data display screen.
Figure 13:
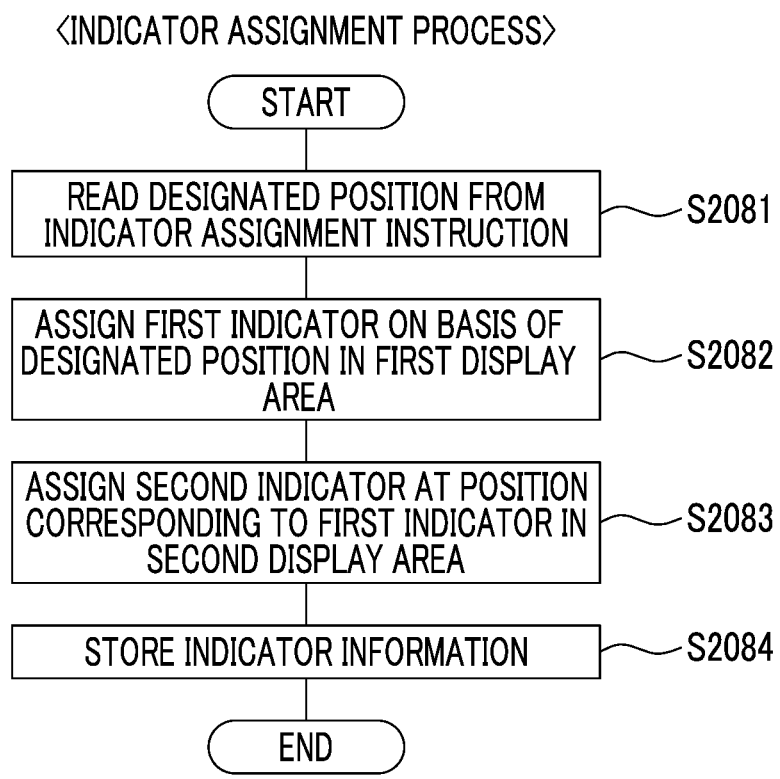
FIG. 13 is a flowchart illustrating a procedure of assigning first and second indicators.

Hereinafter, an operation of the above configuration will be described with reference to FIGS. 12 and 13. In the event that the data display screen 15 is displayed, the viewer software starts up in the client terminal 12. A patient ID is designated in the start-up screen by the doctor, and a distribution request is issued (S1010). The distribution request is transmitted from the client terminal 12 to the data distribution server 11. Assuming that the data distribution server 11 receives the distribution request (S2010), the screen data generation unit 72 extracts the patient ID included in the distribution request, and reads edit information on the designated patient ID from the edit information DB 82. In a case in which there is the edit information on the designated patient ID (Y in S2020), the time-series data TS designated by screen setting information in the edit information is acquired from the server group 13 (S2030). The screen editing unit 73 generates the screen data 15A on the basis of the acquired time-series data TS and edit information (S2040). On the other hand, in the case of a new patient ID, since there is no edit information (N in S2020), the screen data generation unit 72 generates the screen data 15A in an initial setting (S2050).

The data distribution server 11 distributes the generated screen data 15A to the client terminal 12 (S2060). The client terminal 12 reproduces the data display screen 15 on the basis of the received screen data 15A and displays the data display screen 15 on the display 28A (S1020). The client terminal 12 waits for a screen editing operation such as an operation of assigning the first indicator 56 (S1030). In a case in which there is the screen editing operation (Y in S1030), the client terminal 12 issues a screen edit request (S1040).

Assuming that the data distribution server 11 receives the screen edit request (S2070), the screen editing unit 73 performs an editing process according to the screen edit request (S2080) In a case in which there is an indicator assignment instruction in the screen edit request, the screen editing unit 73 reads a designated position from the indicator assignment instruction (S2081). The screen editing unit 73 assigns the first indicator 56 at the designated position in the first display area 41 (S2082). The screen editing unit 73 assigns the second indicator 57 at a corresponding position corresponding to the first indicator 56 in the second display area 42 (S2083). The screen editing unit 73 generates update data in which the first indicator 56 and the second indicator 57 are assigned. After the indicator assignment, the screen editing unit 73 stores indicator information in the edit information DB 82 as edit information on the basis of content of the indicator assignment instruction (S2084).

In the case of a screen edit request other than the indicator assignment instruction, the screen editing unit 73 performs screen editing and generation of update data according to designated content, and stores edit information in the edit information DB 82. The data distribution server 11 distributes the generated update data (S2090). The client terminal 12 updates and displays the data display screen 15 on the basis of the update data (S1020).

In the data display screen 15, the first indicator 56 is displayed in the first display area 41. As illustrated in FIGS. 7 and 8, a first indicator 56 is assigned at a designated position determined to be important by the doctor, such as a position showing a significant change in the time-series data TS such as decrease in blood pressure after medication. Therefore, even in the event that the doctor looks back the time-series data TS of the patient, the doctor can simply find the position determined to be important.

Further, in addition to the first indicator 56, a second indicator 57 is displayed at a position corresponding to the first indicator 56 in the second display area 42. Since the second display area 42 has a longer time scale than the first display area 41, it is possible to simply find the first indicator 56 not displayed in the first display area 41 such as the first indicator 56 assigned in the past, by searching for the second indicator 57 in the second display area 42. Therefore, it is possible to recognize the entire image regarding the important point in time regarding the medical care by confirming the position of the second indicator 57 in the second display area 42 and to simply recognize a detailed change in the time-series data at the important point in time at which the first indicator 56 has been assigned by confirming the first indicator 56 in the first display area 41.

In the case of a patient visiting a hospital or hospitalized over a relatively long period, an acquisition period of the time-series data is also a long period. Since the first display area 41 is an area for confirming a fine change in the time-series data, the time scale is short and a display range of the time-series data is narrow. Therefore, since a proportion that can be displayed in the first display area 41 decreases as an acquisition period of the time-series data increases, the number of first indicators 56 that are not displayed in the first display area 41 increases, and a risk of oversight of the previous important first indicators 56 increases in the event that the time-series data is looked back. According to this example, since the second indicator 57 indicating the presence of the first indicator 56 is displayed in the second display area 42 having a longer time scale, it is possible to reduce a risk of oversight of the important first indicator 56 even in the event that the acquisition period of the time-series data is long. Therefore, the present invention is particularly effective in a case in which a medical care period is relatively long due to hospital visit or hospitalization of patient or an acquisition period of the time-series data is long.

The data distribution server 11 waits for an additional screen edit request after the distribution of the update data (S2100). Assuming that there is the additional screen edit request, the above procedure is repeated.

In the client terminal 12, assuming that the end button 68 of the data display screen 15 is operated, the data display screen 15 ends. The client terminal 12 issues a display end notification (S1050). Assuming that the data distribution server 11 receives the display end notification, the data distribution server 11 performs a termination process. In a case in which the distribution request is received again, the process from S2010 is repeated. The end process is executed in a case in which there is no request from the client terminal 12 for a defined time (so-called timeout), in addition to a case in which the end notification is received.

In this example, since the first indicator 56 is in the form of a tag in which a comment can be input and displayed, a judgment or a thought process of the doctor in the event that the first indicator 56 is assigned, such as a reason for assignment of the first indicator 56 and a meaning of data at the designated position at which the first indicator 56 is assigned, can be input as a memo of a memorandum book. Accordingly, it is convenient at the time of subsequent look-back. The first indicator 56 is not limited to the form of the tag and the comment may be unable to be input. Further, a comment may also be displayed in the second indicator 57.

Further, in this embodiment, the indicator information on the first indicator 56 and the second indicator 57 are not directly added to the time-series data TS, but are included in the edit information created separately from the time-series data TS and stored separately from the server group 13 in which the time-series data TS is stored. In a case in which the indicator information is directly added to time-series data TS, the server group 13 that stores time-series data TS may be required to be remodeled, but in this example, such remodeling is not necessary. It should be understood that, in a case in which the time-series data TS to which the indicator information is added can be stored in the server group 13 or remodeling is allowed, the indicator information may be directly added to the time-series data TS.

Further, in this embodiment, since the data distribution server 11 acquires the time-series data TS from the server group 13 for each distribution request instead of storing the acquired time-series data TS, a storage space for time-series data TS in the data distribution server 11 can be reduced. Further, even in the event that the time-series data TS is stored in the data distribution server 11, it is necessary for at least a difference data to be acquired from the server group 13 for each distribution request in order to update to the recent time-series data TS. Therefore, since there is no great difference in a processing time including a data acquisition time even in the event that the acquired time-series data TS is stored, it is advantageous not to store the time-series data TS as in this example since the storage space can be reduced.

Figure 14:
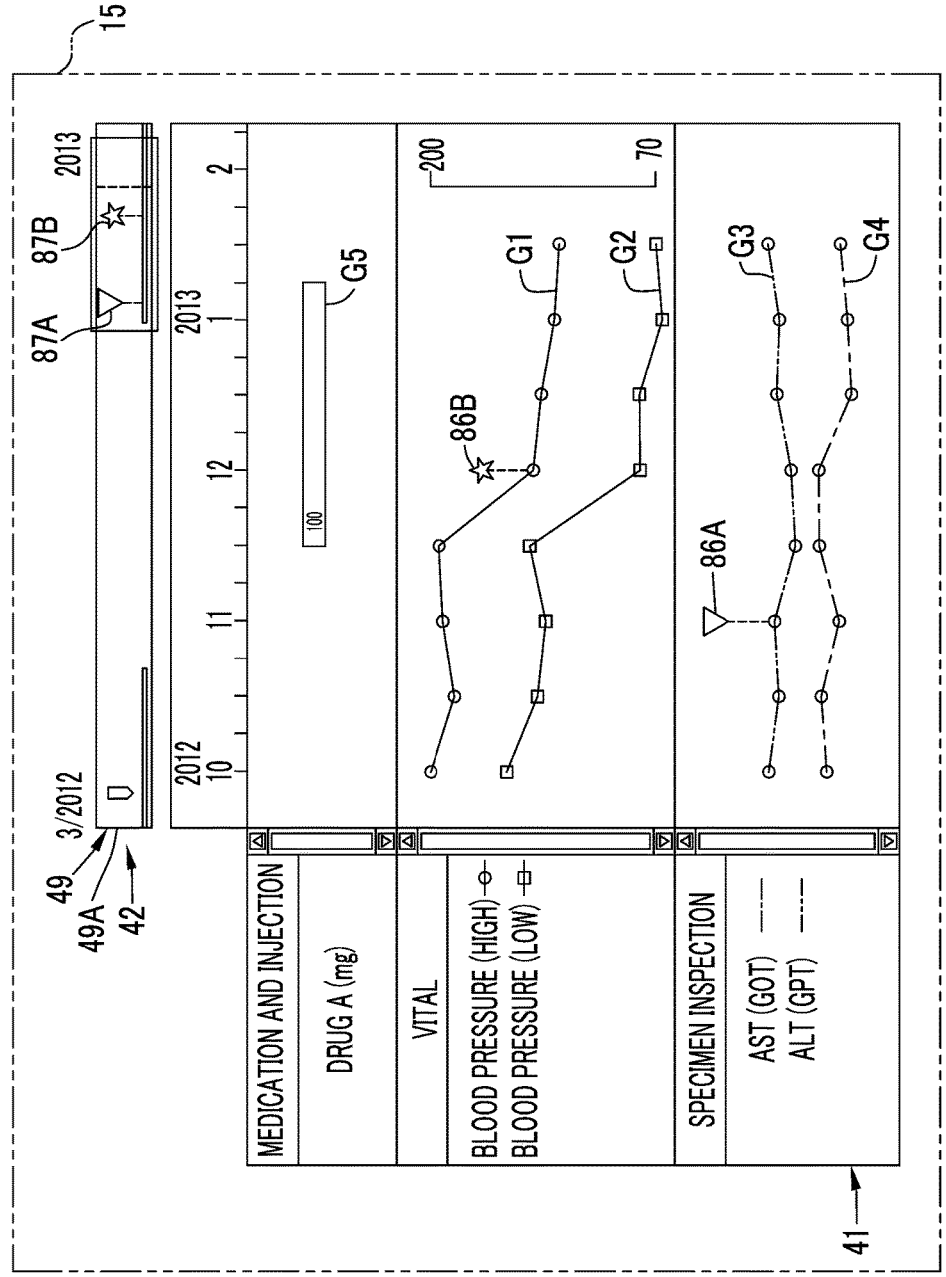
FIG. 14 is an illustrative diagram illustrating an example in which corresponding shapes of the first and second indicators are the same.

As in the example illustrated in FIG. 14, each icon of the first indicator 86 and the second indicator 87 of the data display screen 15 may be changed from among a plurality of types prepared in advance. In this example, the first indicator 86A is an inverted triangular icon, and the first indicator 86B is a star-shaped icon. A type of these icons can be selected arbitrarily. Further, thus, in a case in which the type of icon can be selected from among the plurality of types, it is preferable that the respective icons of the first indicator 86 and the second indicator 87 corresponding thereto are set to the same type of icons. In this example, the first indicator 86A and the second indicator 87A corresponding thereto are set to the same inverted triangular icons, the first indicator 86B and the second indicator 87B corresponding thereto are set to the same star-shaped icons. Thus, even in a case in which there is a plurality of first indicators 86 and second indicators 87, it is possible to confirm a correspondence relationship at a glance.

The icon is selected, for example, in the indicator setting screen 61, and the indicator assignment instruction with icon selection information is transmitted to the data distribution server 11. In the data distribution server 11, data of the icon is stored in the indicator object data in the screen template 81, and the screen editing unit 73 sets a type of icon according to the designation.

[Second Embodiment]

Figure 15:
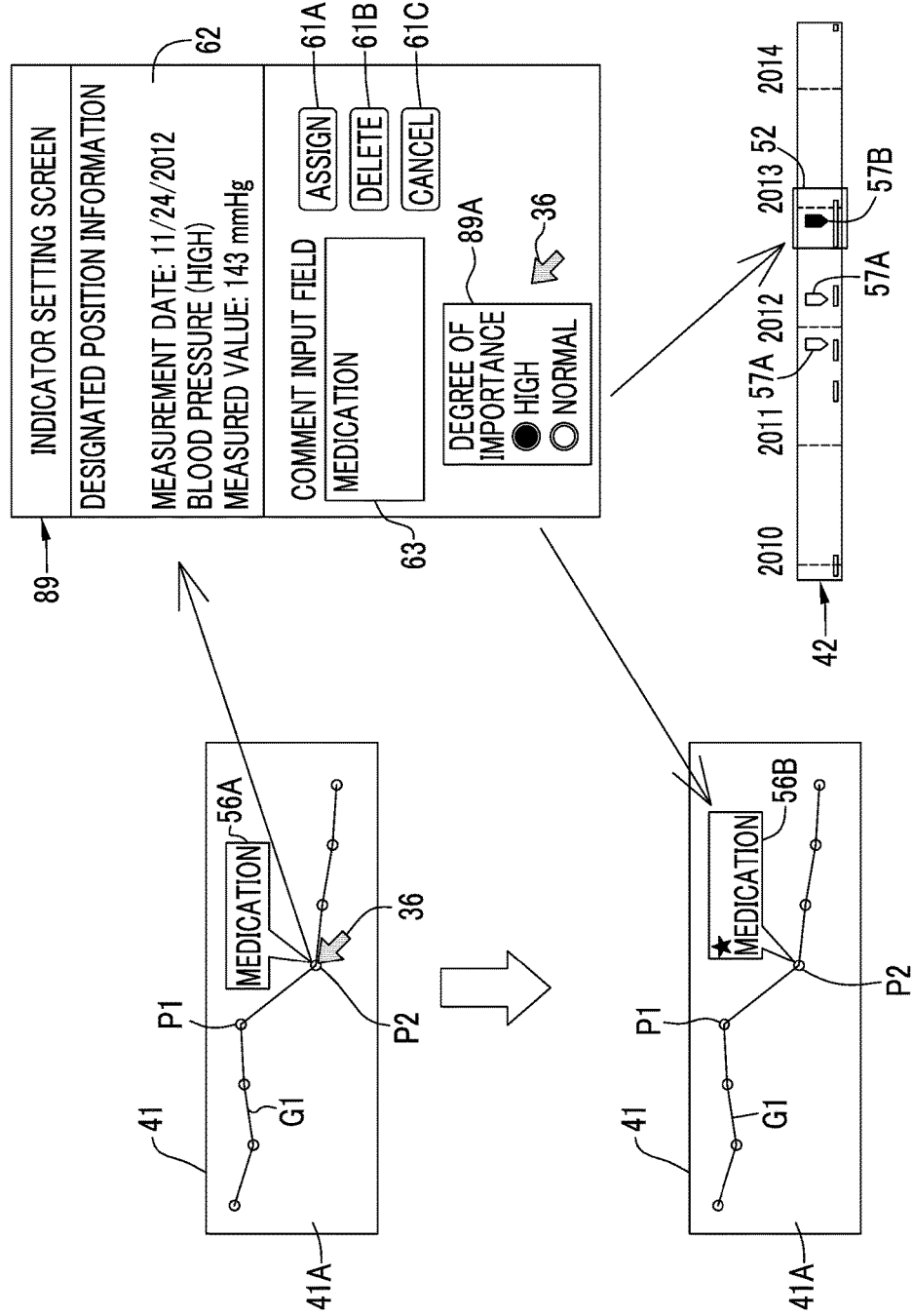
FIG. 15 is an illustrative diagram illustrating a first indicator assignment procedure of a second embodiment in which a degree of importance is set to an indicator.
Figure 16:
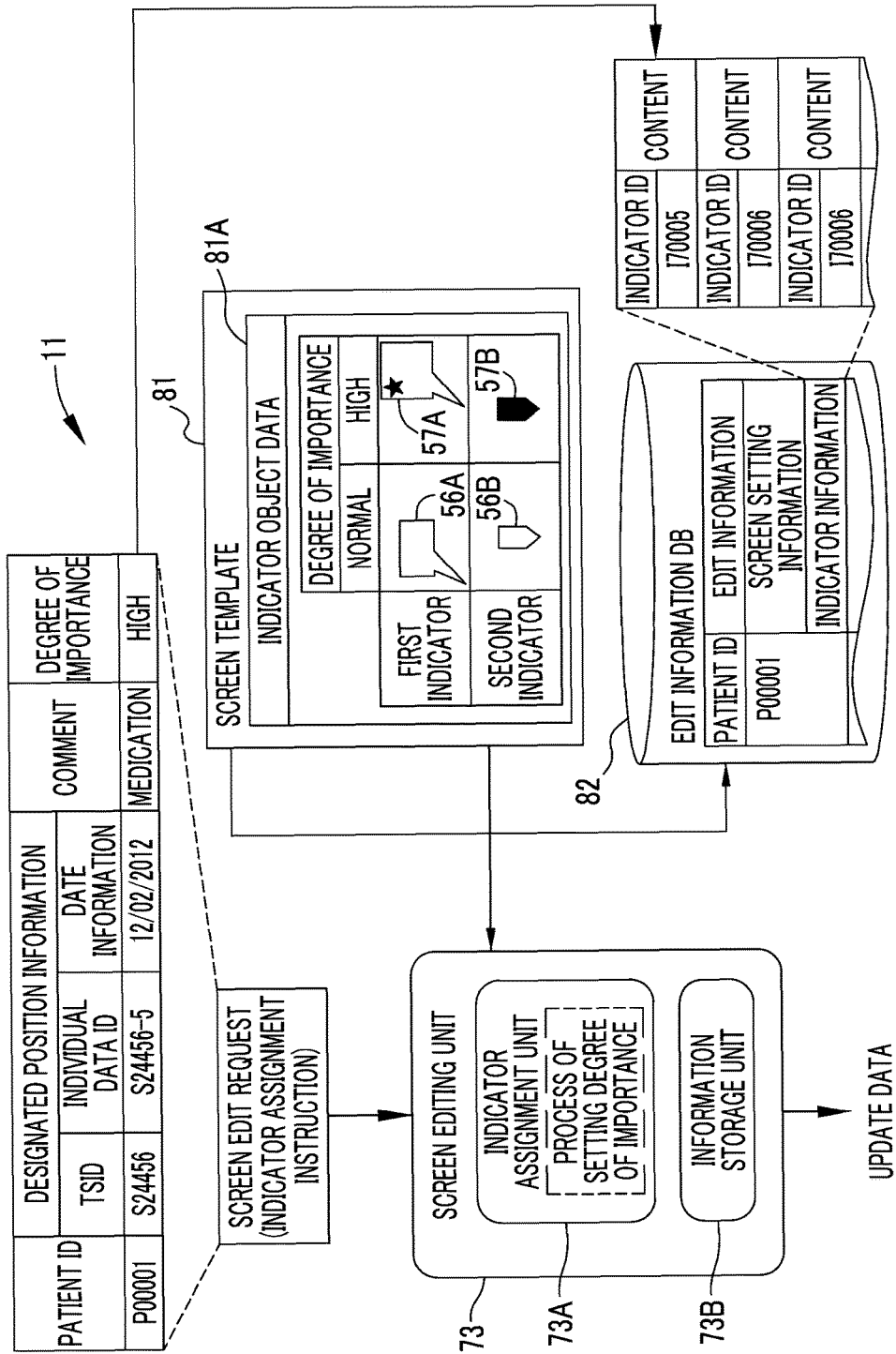
FIG. 16 is an illustrative diagram illustrating a schematic function of a screen editing unit regarding a setting of the degree of importance in the second embodiment.
Figure 17:
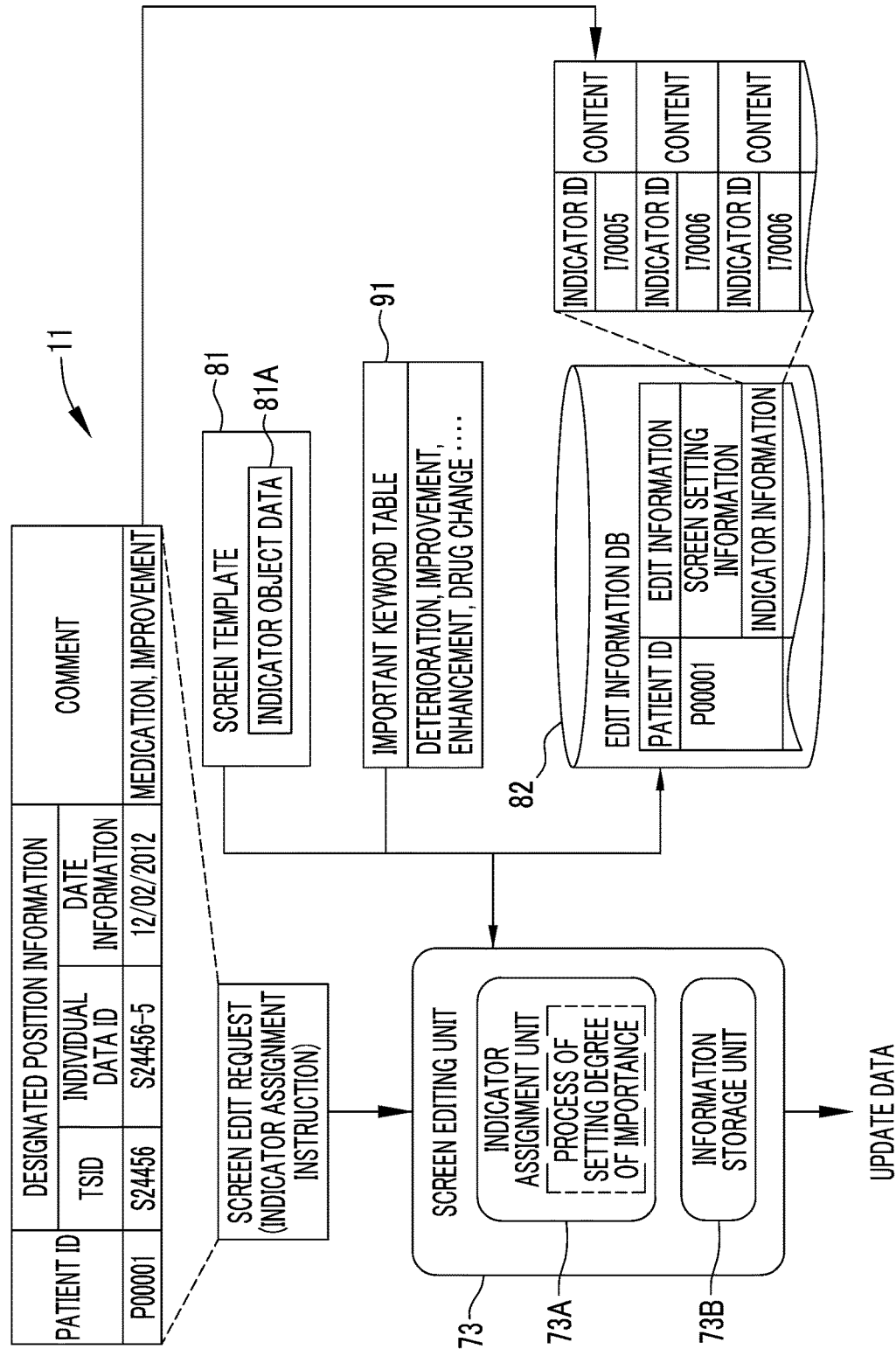
FIG. 17 is an illustrative diagram illustrating an example in which a degree of importance is set in first and second indicators on the basis of a keyword included in a comment.

A second embodiment illustrated in FIGS. 15 to 17 is an embodiment in which a degree of importance can be set for at least one of first and second indicators. Other points are the same as those of the first embodiment, and a difference will be described hereinafter. As illustrated in FIG. 15, a degree-of-importance designation portion 89A for designating a degree of importance is provided in an indicator setting screen 89 of the second embodiment.

In the degree-of-importance designation portion 89A, for example, a radio button for designating a degree of importance of two steps including "high" and "normal" by an operation of the pointer 36 is provided. The first indicator 56A in a case in which "normal" is designated and the first indicator 56B in a case in which "high" is designated have different display modes, and one of the first indicator 56A and 56B is selected according to a designation of the degree of importance. In the first indicator 56B in which the degree of importance "high" is designated, for example, an asterisk is attached to a tagged icon so that the first indicator 56B is more prominent than the first indicator 56A of "normal".

Further, a display mode of the second indicator 57 corresponding to the first indicator 56 is also changed according to the designation of the degree of importance of the first indicator 56. For example, the second indicator 57B corresponding to the first indicator 56B of which the degree of importance is "high" is displayed with a color different from the second indicator 57A of "normal". By reflecting the degree of importance in the second indicator 57, it can be determined whether there is important previous data at a glance, and it is highly convenient since oversight of important items in medical care can be prevented.

In the event that the indicator assignment instruction is performed on the basis of the indicator setting screen 89, an indicator assignment instruction including a designation ("high" in this example) of the degree of importance is transmitted to the data distribution server 11, as illustrated in FIG. 16. The indicator assignment unit 73A of the screen editing unit 73 functions as a degree-of-importance setting unit which performs a process of setting the degree of importance on the basis of the designation of the degree of importance. Indicator object data 81A of each icon of the first indicators 56A and 56B and second indicators 57A and 57B is stored in the screen template 81. The indicator assignment unit 73A selects the indicator object data 81A according to the designation on the basis of the designation of the degree of importance included in the indicator assignment instruction and performs the process of setting the degree of importance. The first indicator 56, the second indicator 57 is assigned according to the degree of importance set.

By performing the setting of the degree of importance in this manner, the first indicator that is particularly important among the first indicators 56 can be confirmed at a glance. Assuming that the confirmation of the first indicator that is important is simplified, efficiency of medical care is improved. Since the number of the first indicators 56 increases assuming that the medical care period is a long period, the setting of the degree of importance is useful as a method of simply selecting the first indicator that is important from among the first indicators.

Further, as illustrated in FIG. 17, the setting of the degree of importance may be performed according to content of the comment input in the indicator setting screen 61. In this case, an important keyword table 91 is provided in the data distribution server 11. The important keyword table 91 is stored in, for example, the storage device 23B (FIG. 10). In the important keyword table 91, an important keyword considered an important comment is set. As the important keyword, for example, a word indicating a change in the time-series data TS such as deterioration, improvement, enhancement, drug change, increase, decrease, and side effects is set. The indicator assignment unit 73A reads the comment input by the doctor from the indicator assignment instruction, collates comments with the important keyword, and determines that the degree of importance is high assuming that the important keyword is included in the comment. In a case in which a comment "improvement" is included as in this example, the indicator assignment unit 73A determines that the degree of importance of the first indicator 56 to be assigned is high. On the other hand, in a case in which the important keyword is not included in the comment, the indicator assignment unit 73A determines that the degree of importance is normal. The degree of importance of the first indicator 56 and the second indicator 57 is set according to such a determination result.

In this example, the degree of importance can be designated in two steps, but may be designated in three or more steps. As a display mode in a case in which the degree of importance is designated in three or more steps, for example, a method of increasing the number of asterisks attached to the first indicator 56 as the degree of importance increases can be considered. Further, as in this example, it is preferable to change the display mode of both of the first indicator 56 and the second indicator 57 according to the degree of importance, but the display mode of one of the first indicator 56 and the second indicator 57 may be changed. This is because one of the first indicator 56 and the second indicator 57 can be found from the other since the first indicator 56 and the second indicator 57 correspond to each other in time. Further, the degree of importance of the second indicator 57 is designated by designating the degree of importance of the first indicator 56, whereas the first indicator 56 may be designated by designating the second indicator 57.

[Third Embodiment]

Figure 18:
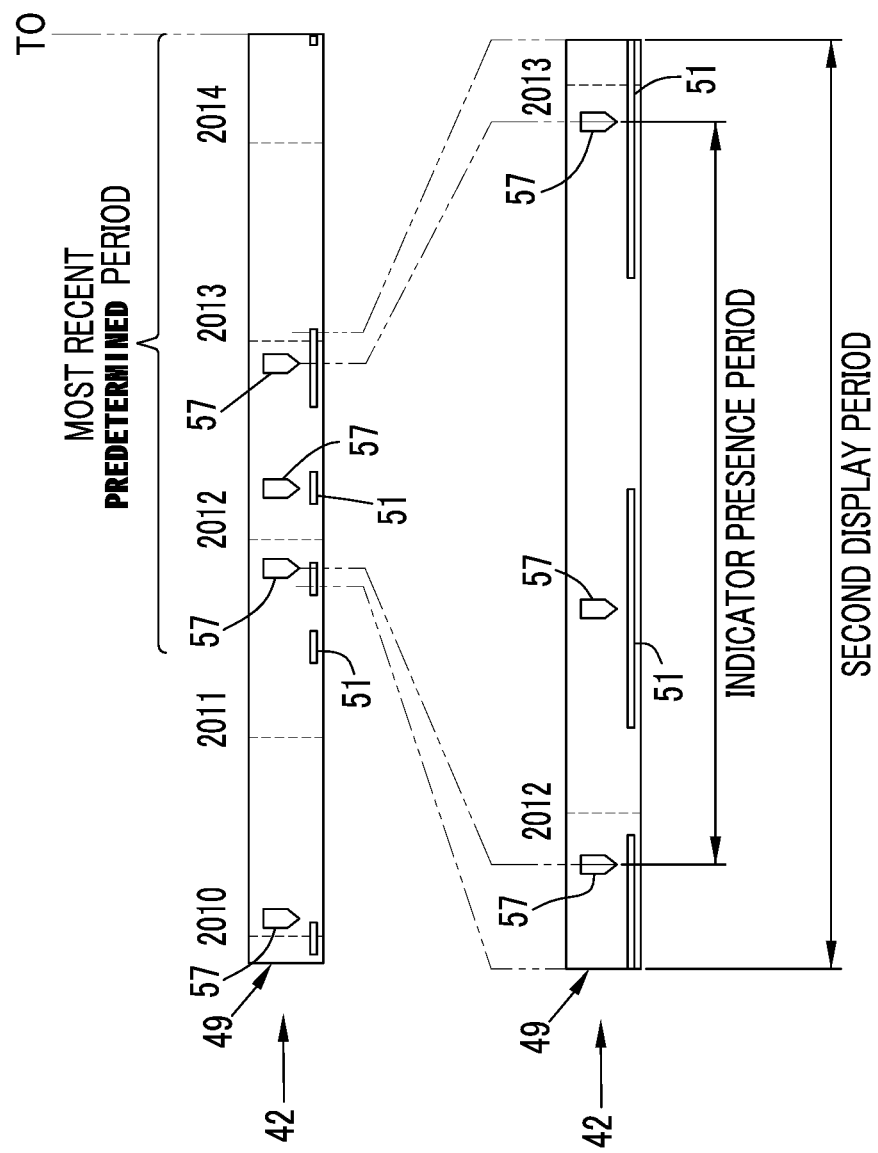
FIG. 18 is an illustrative diagram illustrating a third embodiment in which a second display period is set according to a period in which there is a first indicator.

A third embodiment illustrated in FIG. 18 is an embodiment in which the second display period of the second display area 42 can be set according to a period in which there is the first indicator 56. For example, assuming that a point in time at which the data display screen 15 is displayed in the client terminal 12 is a current point in time T0, the period in which there is the first indicator 56 is extracted from among predetermined period that is most recent from the current point in time T0. In this example, the current point in time T0 is March 2014, and the most recent predetermined period is about 3 years. From this, the period in which there is the first indicator 56 is extracted as an indicator presence period. In this example, the second indicator 57 is present in 2010, but this period is outside the predetermined period, and accordingly, is not included in the indicator presence period to be extracted. The extracted indicator presence period is set as the second display period. As in this example, a margin may be added before and after the indicator presence period, and the indicator presence period to which the margin is added may be set as the second display period.

The setting of the second display period based on the first indicator 56 is realized, for example, by incorporating a function of setting the second display period into the screen data 15A in the data distribution server 11. The client terminal 12 receives the screen data 15A with the function of setting the second display period. The GUI control unit 33 searches for the position at which the first indicator 56 has been assigned in the range of the time-series data TS included in the received screen data 15A, and extracts the indicator presence period. The extracted indicator presence period is set as the second display period of the second display area 42. Further, as another method, a method transmitting a request to set the second display period from the client terminal 12 to the data distribution server 11, changing the second display period of the second display area in the screen editing unit 73, and distributing the changed screen data 15A to the client terminal 12 may be used.

Thus, it is possible to simply adjust the second display period to be an appropriate period by setting the second display period according to the period in which there is the first indicator 56. Since the first indicator 56 is intended to be assigned at an important position, assuming that at least only a period in which there is the first indicator 56 is set as the second display period of the second display area 42, a minimum required range can be covered. On the other hand, assuming that the second display period is unnecessarily long, visibility is likely to be degraded. For example, a display of the second indicator 57 corresponding to the first indicator 56 becomes small. Therefore, it is possible to simply adjust the second display period to be an appropriate period by setting the second display period according to the presence period of the first indicator 56.

In this example, an extraction range of the indicator presence period is limited to the most recent predetermined time period from a current point in time T0, but the extraction range is not limited to the most recent predetermined period and, for example, an entire period in which there is the time-series data TS may be used as the extraction range. Further, although the period in which there is the first indicator 56 is extracted as the indicator presence period and the extracted indicator presence period is set as the second display period, a period including a period in which there are the current point in time T0 and the first indicator 56 may be set as the second display period. This is because, even in the event that the first indicator 56 is not assigned at the current point in time T0, it is necessary to confirm the current point in time T0 since data at the current point in time T0 is recent data, and it is necessary to compare the recent data with the previous first indicator 56 or the previous second indicator 57. Since time-series data indicating a recent state transition of the patient and content of medical care performed on the patient may not be included at the current point in time T0, a period including the period in which there are the recent time-series data and the first indicator 56 may be set as the second display period.

[Fourth Embodiment]

Figure 19:
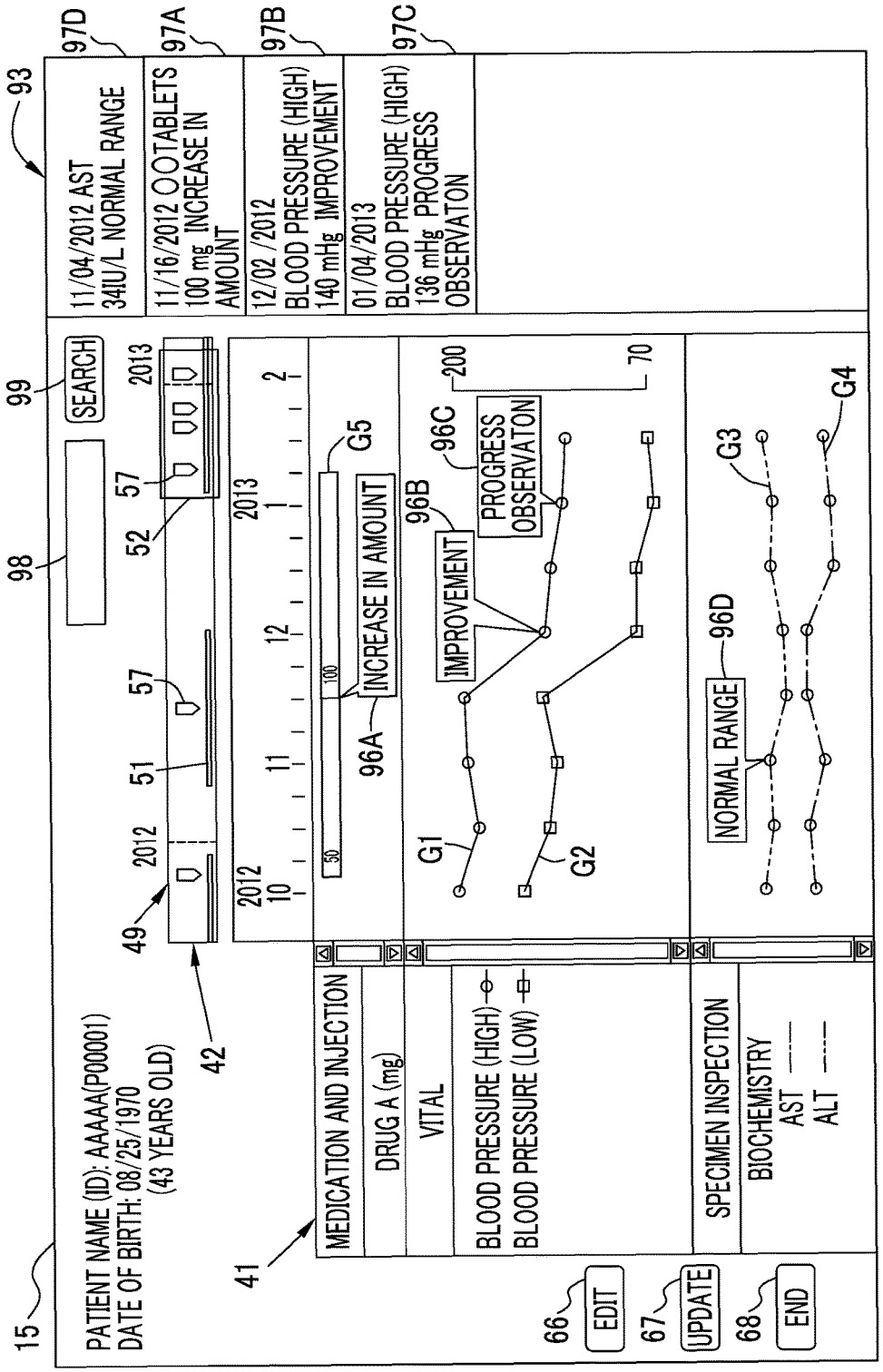
FIG. 19 is an illustrative diagram illustrating an example of a data display screen in a fourth embodiment in which information on the first indicator is displayed as a list.
Figure 20:
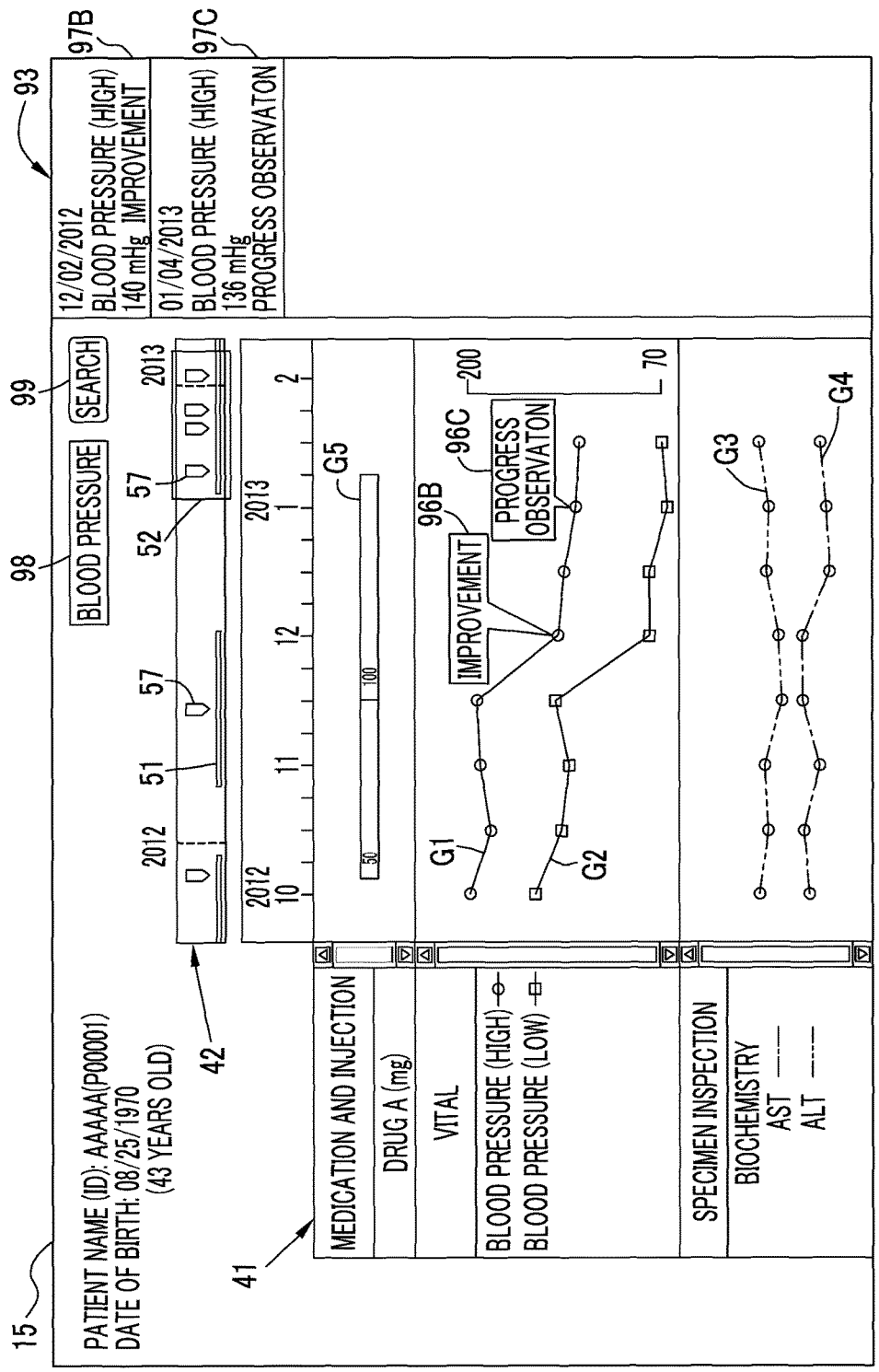
FIG. 20 is an illustrative diagram illustrating an example of a data display screen in which some of first indicators are hidden.
Figure 21:
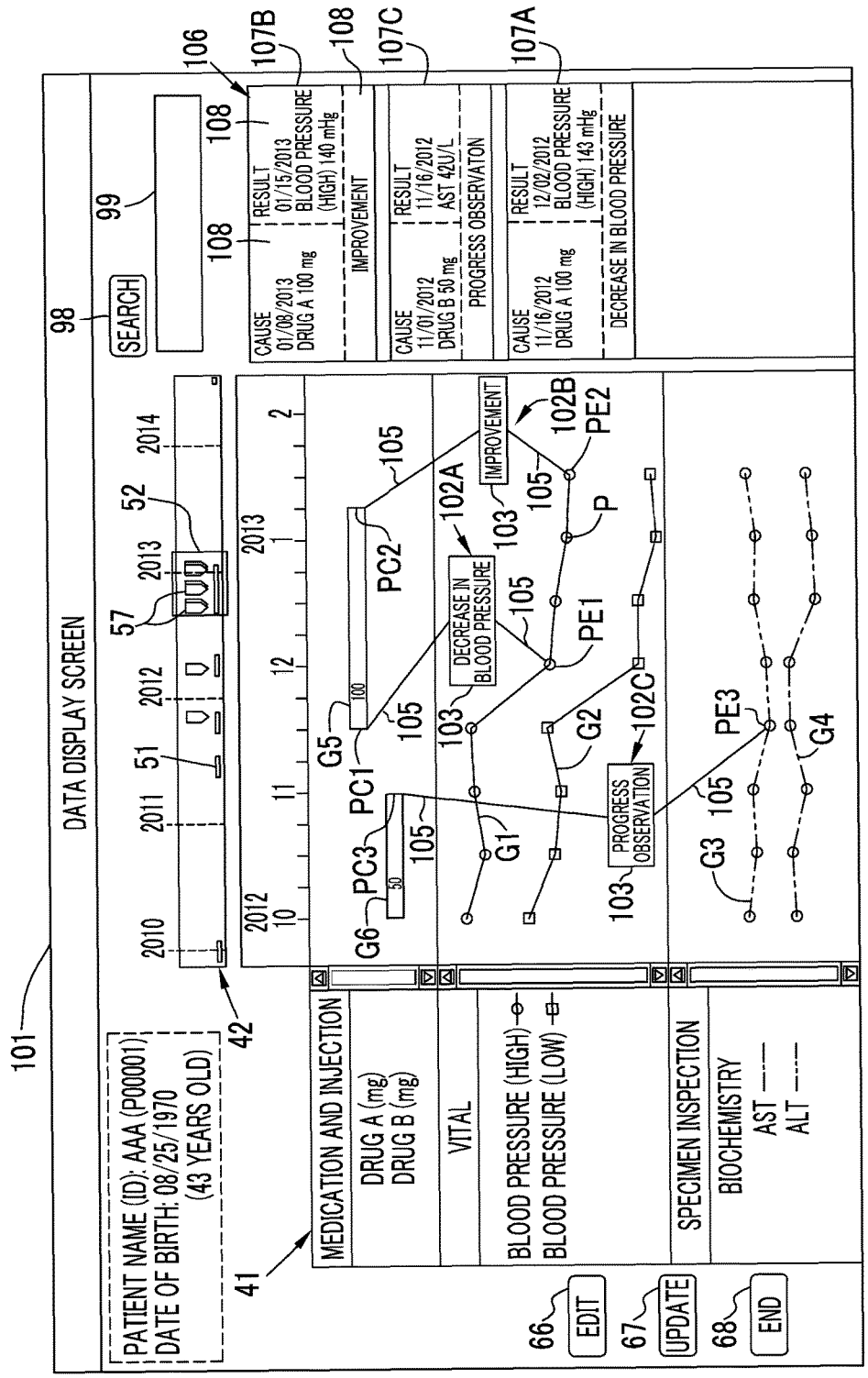
FIG. 21 is an illustrative diagram illustrating an example of a data display screen in a fifth embodiment in which an association indicator is assigned to time-series data of the first display area.

A fourth embodiment illustrated in FIGS. 19 and 20 is an example in which a list display area 93 for displaying content of the comment of the first indicator as a list is provided in a data display screen 15. Other points are the same as those in the first embodiment, and a difference will be described hereinafter.

As illustrated in FIG. 19, the data display screen 15 of the fourth embodiment includes a list display area 93, in addition to a first display area 41 and a second display area 42. Content of a plurality of first indicators assigned to the time-series data TS is listed in the list display area 93. For example, a plurality of content display fields 97A to 97D for displaying, for each indicator, the content for each of a plurality of first indicators 96A to 96D displayed in the first display area 41 is provided in the list display area 93. The respective content display fields 97A to 97D are arranged, for example, in the form of a list in a vertical direction.

The content of the first indicator 96 displayed in the content display field is information on the designated position at which the first indicator 96 is assigned and, specifically, information such as individual data (for example, measured value, inspection data, or dosage) of the designated position, date of the individual data, a name ("blood pressure (high)", and "AST") of the individual data, and an input comment. For example, a first indicator 96D is an indicator that is assigned to time-series data TS of "AST", and date of the designated position at which the first indicator 96D is assigned, a name ("AST") of individual data, and a comment ("normal range") input to the first indicator 96D are displayed as content of the first indicator 96D in the content display field 97D corresponding to the first indicator 96D. Similarly, content of the first indicators 96A to 96C corresponding to the content display field 97A to 97C is displayed in the content display field 97A to 97C.

In this example, a content display field 97 corresponding to the first indicator 96 displayed in the first display area 41 is displayed in the list display area 93. In a case in which the first display period of the first display area 41 is changed by a scroll operation, the displayed first indicator 96 is also changed. Therefore, it is preferable for the content display field 97 of the list display area 93 to be also changed in conjunction with the change in the first indicator 96 displayed in the first display area 41.

Further, a target of the content display field 97 displayed in the list display area 93 may be the second indicator 57 displayed in the second display area 42 instead of the first indicator 96 displayed in the first display area 41.

Further, in this example, the respective content display fields 97A to 97D are sorted by date and displayed in the list display area 93. An example of a sort condition may be an order of assignment of the first indicator 96, in addition to the date. The sort condition may be selected.

The change or the sort in conjunction with the first display period of the respective content display fields 97A to 97D is executed, for example, by the GUI control unit 33 of the client terminal 12 on the basis of the screen data 15A, without making a request from the client terminal 12 to the data distribution server 11, in a range of the first indicator 96 included in the screen data 15A received by the client terminal 12. In a range not included in the screen data 15A, the update data from the data distribution server 11 is requested. It should be understood that the client terminal 12 may perform no sort or change and transmit a sort request or a change request to the data distribution server 11. In this case, the screen editing unit 73 performs the sort or the change, and distributes update data of the sorted or changed screen from the data distribution server 11 to the client terminal 12.

Further, a function of searching for the first indicator 96 using a keyword is provided in the data display screen 15 of the fourth embodiment. The content display field 97 corresponding to the first indicator 96 extracted by the search is displayed in the list display area 93. The designated position at which the first indicator 96 is assigned corresponds to the individual data of time-series data TS. As illustrated in FIG. 2, the individual data includes attribute information. It is possible to perform keyword search for the first indicator 96 using the attribute of the individual data.

As illustrated in FIG. 20, in the event that, for example, "blood pressure" is input as a keyword, the first indicators 96B and 96C including "blood pressure" in the attribute are extracted, and the content display fields 97B and 97C corresponding to the extracted first indicators 96B and 96C are displayed in the list display area 93. In this example, the display of the first display area 41 is also changed to display of only the extracted first indicators 96B and 96C in conjunction with the display of the list display area 93. Accordingly, it is possible to simply confirm the content of the first indicator 96 that the doctor desires to confirm. Further, since the unnecessary first indicator 96 is hidden and only the necessary first indicator 96 is displayed, the first indicator 96 is legible.

The keyword input field 98 is an input field for inputting a keyword for searching for the first indicator 96. Assuming that the keyword is input and the search button 99 is operated, the GUI control unit 33 searches for the first indicator 96 included in the received screen data 15A. Indicator information of the first indicator 96 or time-series data TS that is a set of individual data is included in the screen data 15A. The GUI control unit 33 extracts the first indicator 96 of an attribute matching the input keyword from among the individual data corresponding to the first indicator 96. The content display field 97 corresponding to the extracted first indicator 96 is displayed in the list display area 93, and a display of the first display area 41 is also changed in conjunction with the display of the list display area 93.

In the example of FIGS. 19 and 20, the search range of the first indicator 96 includes the first indicator 96 displayed in the first display area 41. It should be understood that, the search range of the first indicator 96 is not limited to the first indicator 96 displayed in the first display area 41, and it is preferable for the search range of the first indicator 96 to include all of the time-series data TS regarding the patient ID. In this case, since all of the time-series data TS is highly not to be included in the screen data 15A received by the client terminal 12, it is preferable for such a search process to be executed by the data distribution server 11 according to a search request from the client terminal 12.

Further, the first indicator 96 displayed in the list display area 93 may be set by selecting the attribute in place of or in addition to the search. For example, a selection button for selecting an attribute list in which a plurality of attributes are displayed and the attribute in the list is displayed, and an attribute is selected from the list instead of inputting a keyword. Accordingly, only the content display field 97 of the first indicator 96 of the selected attribute among the plurality of first indicators 96 is displayed in the list display area 93.

Thus, the first indicator 96 is associated with the attribute of the time-series data TS to which the first indicator 96 is assigned, and in the list display area 93, it is possible to narrow down the first indicators 96 to be displayed from the plurality of first indicators 96 according to the attribute. Such a narrowing function is effective in a case in which the number of first indicators 96 is large or in a case in which there is an attribute of interest.

[Fifth Embodiment]

A fifth embodiment illustrated in FIGS. 21 to 25 is an example in which the first indicator is in the form of an association indicator. A first indicator 56 of the first embodiment is an indicator assigned at one designated position, whereas the association indicator is an indicator assigned to indicate that a plurality of designated positions that have been designated are associated positions. As shown in the data display screen 101 in FIG. 21, each association indicator 102 includes a tag 103, and a connection line 105 that connects two designated positions. The tag 103 is an indicator in which a comment can be input and displayed.

As described above, a causal relationship may be recognized between a plurality of pieces of time-series data TS, like a result of a decrease in blood pressure occurring due to a cause of medication. In such a case, using the association indicator 102, a cause position corresponding to the cause and a result position corresponding to the result can be displayed as associated positions.

In the association indicator 102A, a start of a medication period of the graph G5 of medication (drug A) is designated as a cause position PC1, and in the graph G1 of blood pressure (high), a position at which the decrease in blood pressure is recognized is designated as a result position PE1. The cause position PC1 and the result position PE1 are connected by the connection line 105, and accordingly, the relevance is shown. Further, a comment "decrease in blood pressure" is input to the tag 103 of the association indicator 102A and displayed.

In an association indicator 102B, an end period of the medication period of the graph G5 of medication (drug A) is designated as a cause position PC2, and a position at which it is observed that the blood pressure is stabilized as a small value and improvement is confirmed in the graph G1 of blood pressure (high) is designated a result position PE2. Each position is connected by a connection line 105, and "improvement" which is a finding of the doctor is input to the tag 103 of the association indicator 102B and displayed.

Similarly, in an association indicator 102C, an end period of the medication period of the graph G6 of medication (drug B) is designated as a cause position PC3, and a point of the graph G3 of "AST" is designated a result position PE3. Each position is connected by a connection line 105. In the tag 103 of the association indicator 102C, a comment "progress observation" is input and displayed. Thus, assuming that a causal relationship can be once confirmed even in a case in which a definitive judgment cannot be performed for the causal relationship, assignment of the association indicator 102C with a comment "progress observation" facilitates confirmation at the time of subsequent look-back.

Thus, using the association indicator 102, it is possible to simply recognize the causal relationships between a plurality of pieces of time-series data TS. In medical care, the association indicator is very useful to recognize the causal relationship on the basis of a plurality of items of data such as the measured values and the inspection values and determine the next medical care plan.

Further, in a case in which the association indicator 102 has been assigned, the second indicators 57 are displayed at a plurality of designated positions of the cause position and the result position in the second display area 42. Further, content display fields 107A to 107O corresponding to the association indicators 102A to 102O are displayed in the list display area 106. In the case of the content display field 107 corresponding to the association indicator, content regarding the two designated positions of the cause position and the result position is displayed. The content display field 107 is partitioned into three sub-display fields 108, and content of the cause position, content of the result position, and the comment input to the tag are displayed in each sub-display field 108. Since the cause position and the result position are distinguished by the sub-display fields 108 and displayed, it is possible to confirm the content of the cause position and the result position at a glance.

Figure 22:
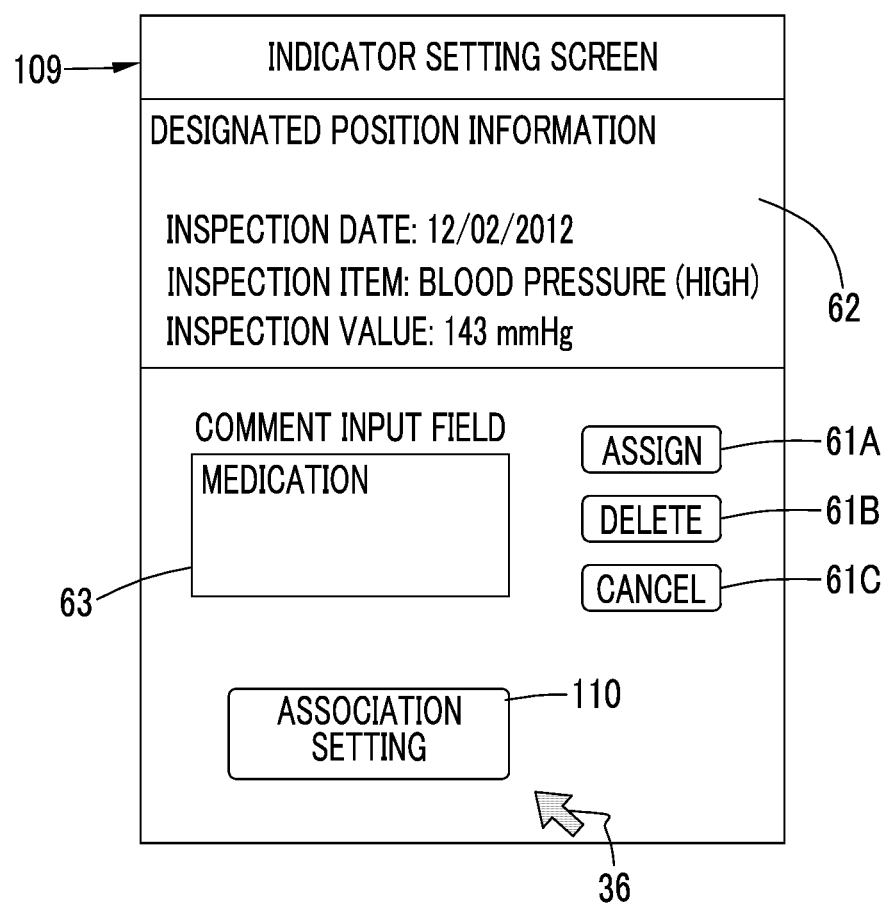
FIG. 22 is an illustrative diagram illustrating an example of an indicator setting screen in which an association setting button is provided.

An assignment operation and process of such an association indicator 102 is performed as follows, for example. Similar to the first indicator 56 of the first embodiment, assuming that any one designated position of the time-series data TS (graph G) is designated by the pointer 36 and a click operation is performed, an indicator setting screen 109 illustrated in FIG. 22 is opened. In the indicator setting screen 109, an association setting button 110 is provided. The other configuration is the same as that of the indicator setting screen 61 illustrated in FIG. 9. In the indicator setting screen 109, it is also possible to assign the first indicator 56 to the designated position in a case in which the association setting is not performed.

Figure 23A:
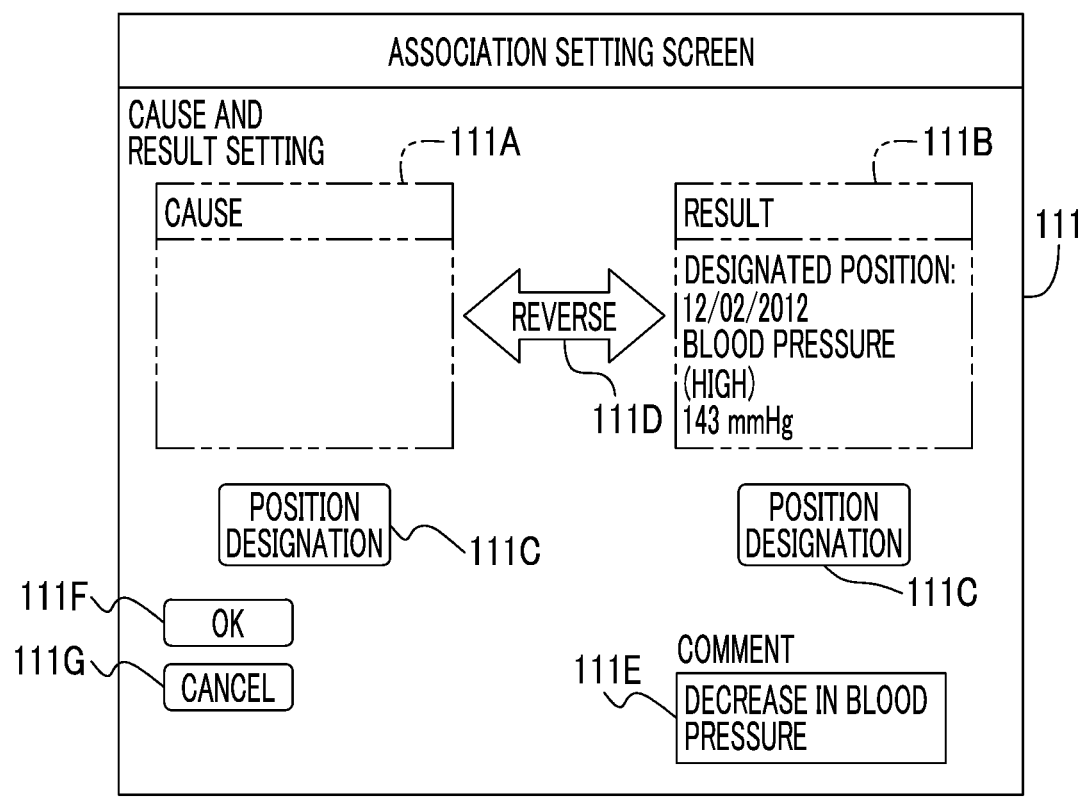
FIG. 23A is an illustrative diagram illustrating an association setting screen in a state in which only a result position is designated.

Assuming that the association setting button 110 is operated with the pointer 36, an association setting screen 111 illustrated in FIG. 23A is opened. The association setting screen 111 includes an information display field 111A, an information display field 111E, a position designation button 111C, a reverse button 111D, a comment input field 111E, an OK button 111F, and a cancel button 111G. Information on the individual data of the cause position and the result position in the time-series data TS is displayed in the information display field 111A and the information display field 111B.

Figure 23B:
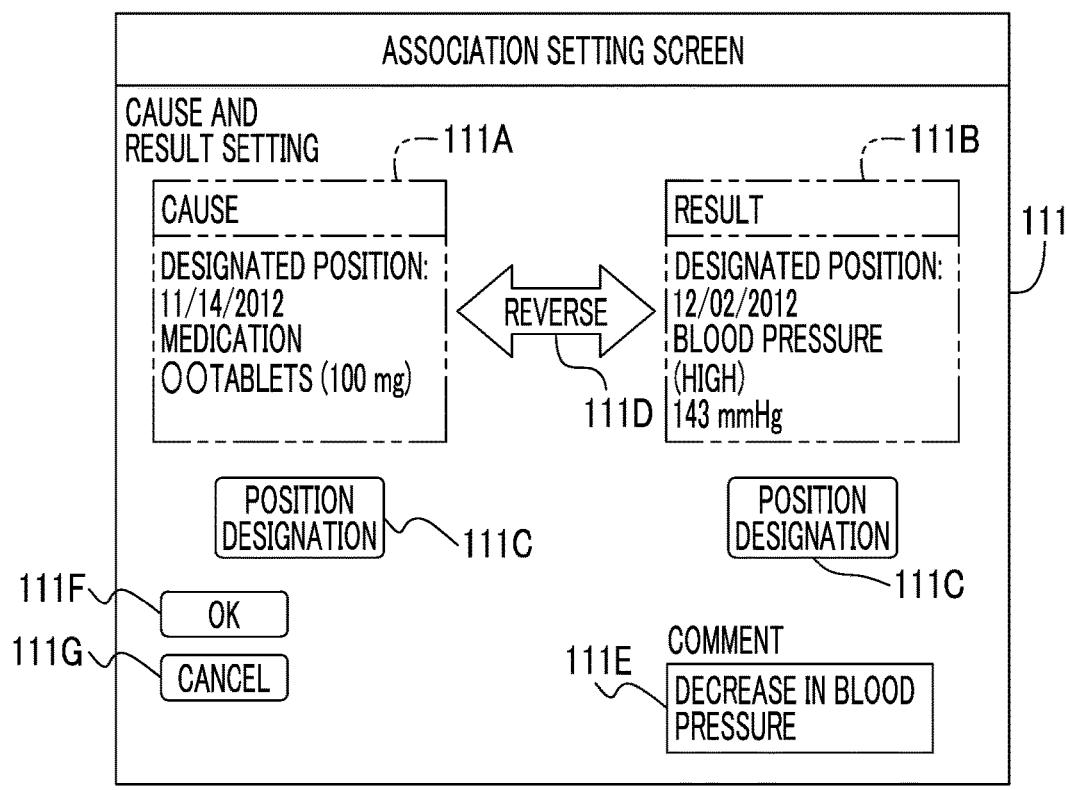
FIG. 23B is an illustrative diagram illustrating the association setting screen in a state in which a cause position and a result position are designated.

As illustrated in FIG. 23A, in a case in which only one of the cause position and the result position is specified, information is displayed in only one of information display fields 111A and 111B. In this example, for example, information on the result position is displayed in the information display field 111B. Assuming that a position designation button 111C is operated, another designated position can be designated. Assuming that another point on the time-series data TS is designated by the pointer 36, information on another designated position is displayed as illustrated in FIG. 23B. A reverse button 111D is an operation button for switching between the positions by reversing the cause position and the result position.

A comment that is displayed in the tag 103 is input to the comment input field 111E. In the event that the OK button 111F is operated, the association indicator 102 is assigned with the set content. The cancel button 111G is a button for canceling the input content. Assuming that the input of the association setting ends and an assignment button 64 of the indicator setting screen 109 is operated, the screen edit request including the indicator assignment instruction is transmitted to the data distribution server 11.

Figure 24:
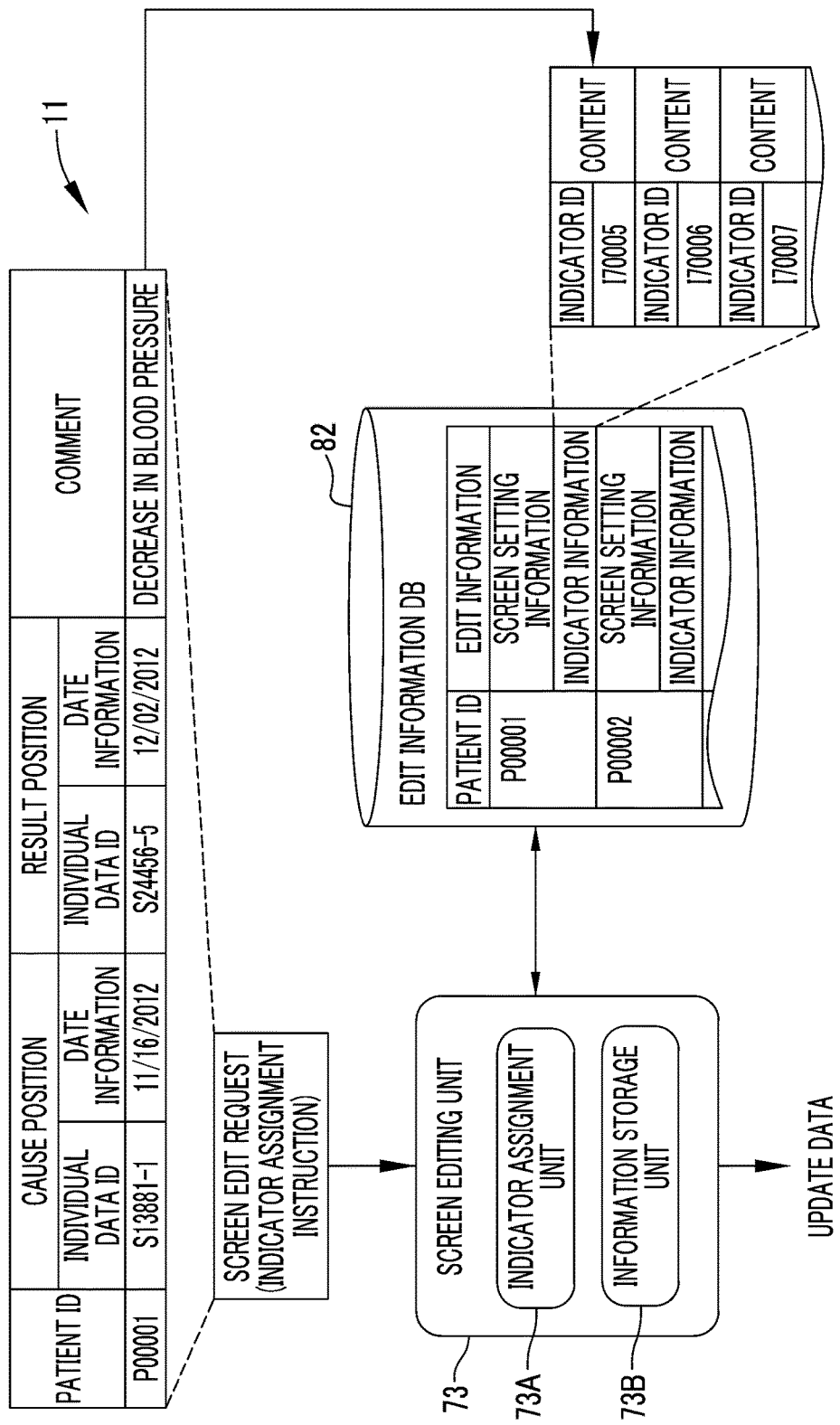
FIG. 24 is an illustrative diagram illustrating a schematic function of a screen editing unit regarding association indicator assignment.

As illustrated in FIG. 24, an indicator assignment instruction including information on the cause position and the result position is transmitted to the data distribution server 11. The association indicator 102 is assigned to the screen editing unit 73 on the basis of this indicator assignment instruction. The indicator assignment unit 73A specifies a position at which the association indicator 102 is assigned in the first display area 41 on the basis of the information on the cause position and the result position, assigns the association indicator 102 to the designated position, and generates update data. The information storage unit 73B stores information on the assigned association indicator 102 in the edit information DB as indicator information.

Figure 25:
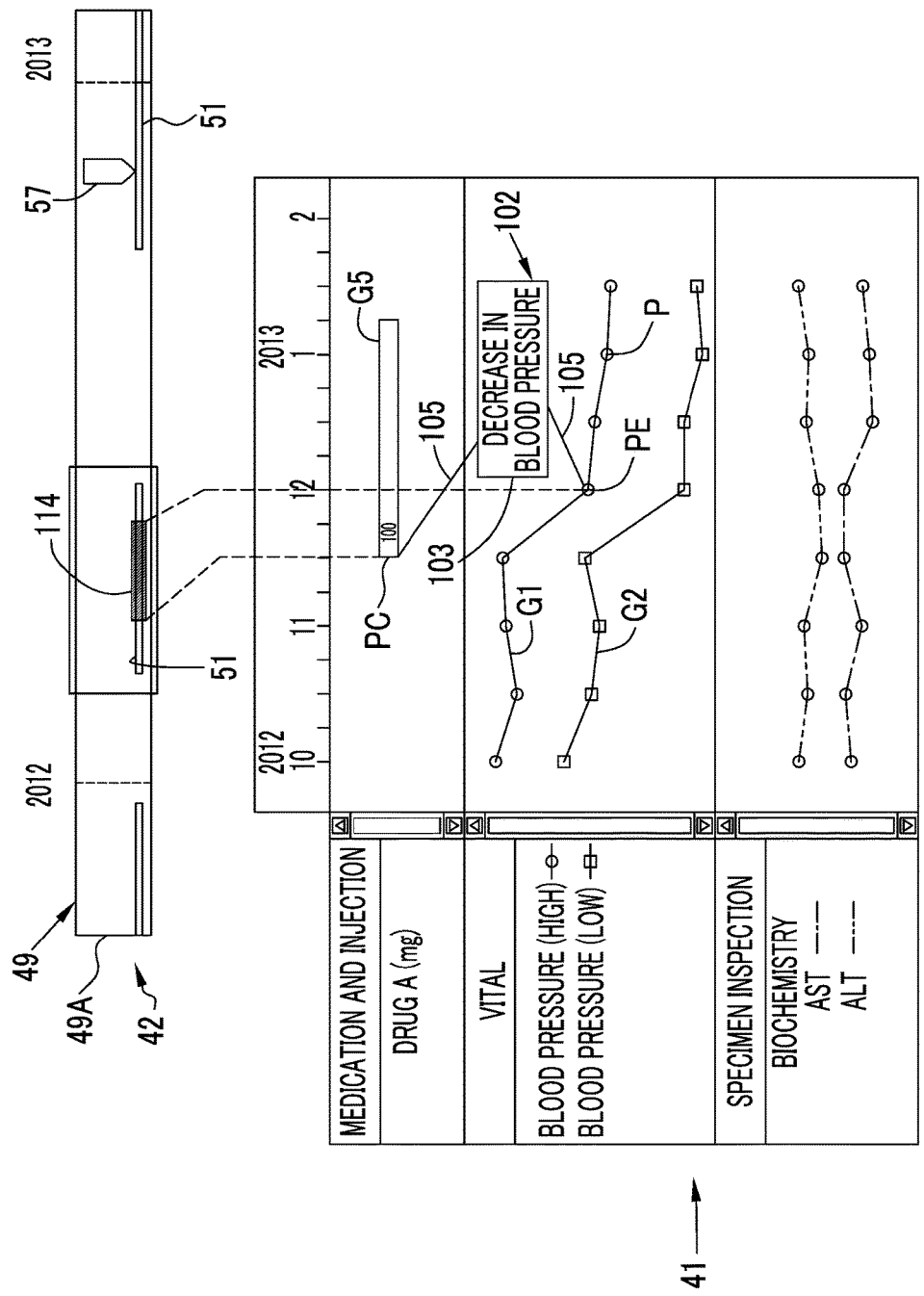
FIG. 25 is an illustrative diagram illustrating another example of a second indicator for association indicator assignment.

In a case in which the association indicator 102 has been assigned, the second indicator may be assigned as one indicator indicating a period among a plurality of designated positions of the clause position and the result position, like a second indicator 114 illustrated in FIG. 25, instead of separately assigning the second indicators displayed in the second display area 42 at the cause position and the result position.

Figure 26:
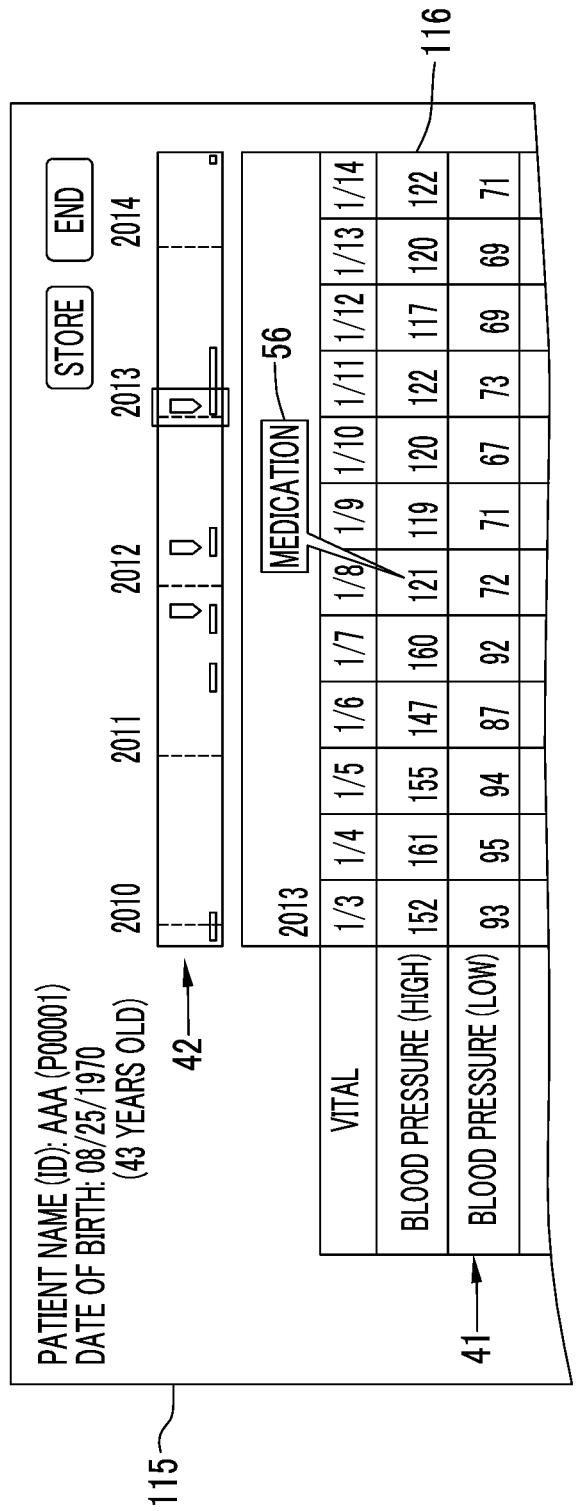
FIG. 26 is an illustrative diagram illustrating an example in which time-series data is displayed in a first display area in a table format.

Although the example in which the time-series data TS is displayed as a graph has been shown in each embodiment, the display form may be displayed in a table format, as illustrated in FIG. 26. In a table 116 in FIG. 26, respective pieces of time-series data TS of blood pressure (high) and blood pressure (low) are arranged in a vertical direction in a first display area 41 of a data display screen 115, and measured values that are individual data of each piece of time-series data TS are arranged in a horizontal direction in time series. A first indicator 56 may be assigned to the individual data or a cell of each piece of the individual data and displayed, as illustrated. Both of a graph and a table may be displayed in the first display area 41.

Although the example in which the first display area and the second display area are a plurality of areas assigned within one screen has been described in each embodiment, for example, the respective areas may be a plurality of separated independent display screens, like a multi-window format. In short, the first display area and the second display area may be in any format as long as the display areas can be displayed in parallel on a screen of a display.

Although the data output device of the present invention has been described as the form of the data distribution server 11 that distributes screen data of the data display screen on the basis of a request from the client terminal 12 in each embodiment, it should be understood that the client terminal 12 may be the data output device in place of the data distribution server 11. In this case, the client terminal 12 accesses the server group 13, acquires the time-series data, and generates the screen data of the data display screen. The client terminal 12 outputs the generated screen data to the display and displays the screen data on the display. In this case, the data output device may include the display.

Various modifications of a hardware configuration of a computer system such as the client terminal 12 or the data distribution server 11 can be made. For example, the data distribution server 11 can include a plurality of server computers separated as hardware in order to improve processing capacity or reliability. Thus, the hardware configuration of the computer system can be appropriately changed according to required performance, such as processing capability, safety, and reliability. Further, it should be understood that a program such as the edit information DB 82 or the AP 30, as well as the hardware, can be made redundant or can be distributed and stored in a plurality of storage devices in order to ensure safety or reliability.

Further, although the data distribution server 11 has been described in a form that the data distribution server 11 is used within one medical facility in each embodiment, the data distribution server 11 may be in a form in which the data distribution server 11 is available to a plurality of medical facilities.

Figure 27:
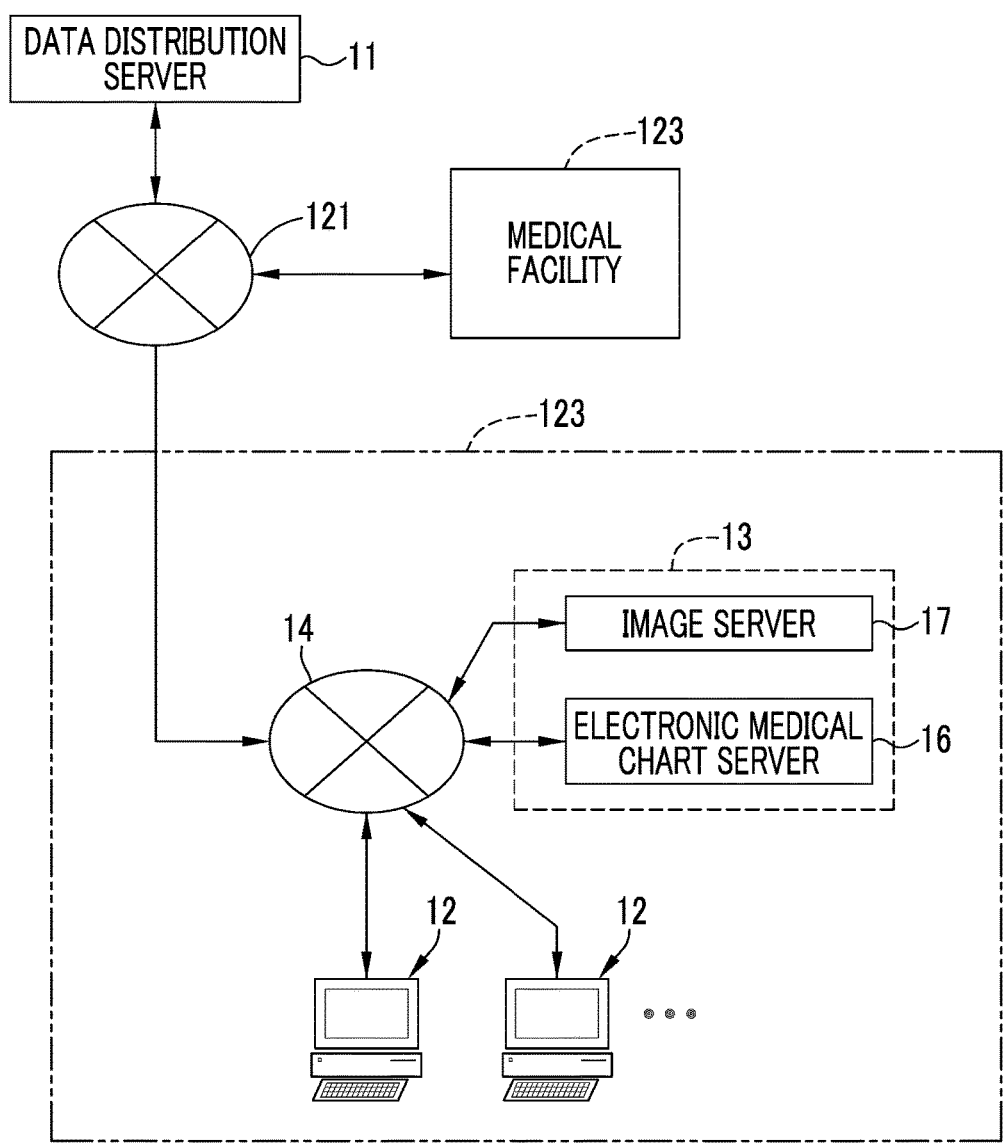
FIG. 27 is an illustrative diagram illustrating a configuration of a medical information system in which a data distribution server is arranged outside a medical facility.

Specifically, in each embodiment, the data distribution server 11 is in the form in which the client terminal 12 installed in the one medical facility is connected to the data distribution server 11 to be able to communicate over the network 14 such as a LAN, and the data distribution server 11 provides an application service regarding the distribution of the screen data on the basis of the request from the client terminal 12. In order for the data distribution server 11 to be available to a plurality of medical facilities, for example, the data distribution server 11 is connected to be able to communicate with the client terminals 12 installed in the plurality of medical facilities 123, for example, over a Wide Area Network (WAN) 121 such as the Internet or a public communication network, as illustrated in FIG. 27. The data distribution server 11 receives the requests from the client terminals 12 in the plurality of medical facilities 123, and provides the application service regarding the distribution of the screen data to each client terminal.

An installation place or an operating subject of the data distribution server 11 in this case, for example, may be a data center different form the medical facility 123 or may be one of the plurality of medical facilities 123. Further, in a case in which a WAN is used, it is preferable that a Virtual Private Network (VPN) is constructed or a communications protocol having a high security level such as Hypertext Transfer Protocol Secure (HTTPS) is used in consideration of information security.

Figure 28:
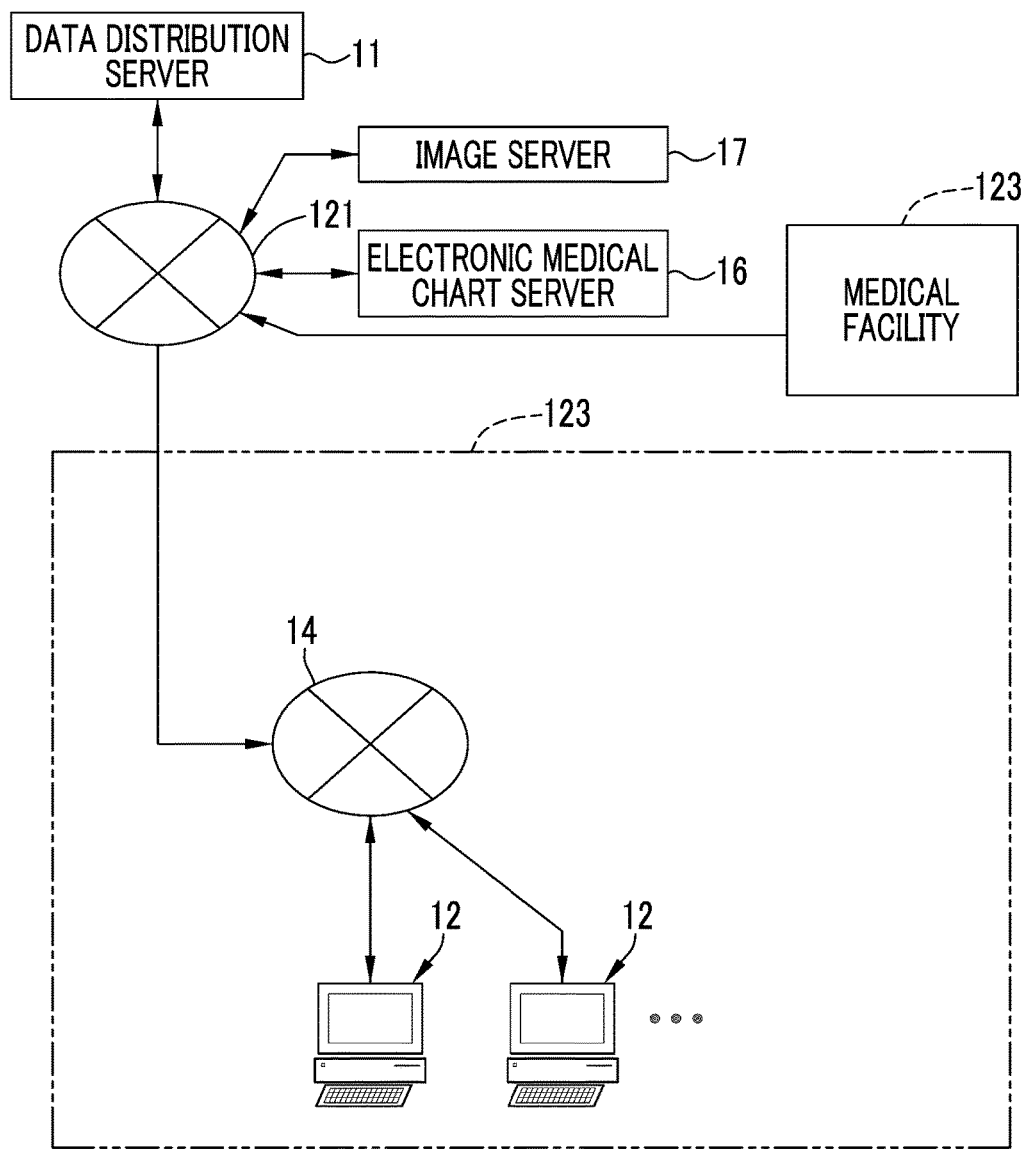
FIG. 28 is an illustrative diagram illustrating a configuration of a medical information system in which a data distribution server, an electronic medical chart server, and an image server are arranged outside a medical facility.
Figure 29:
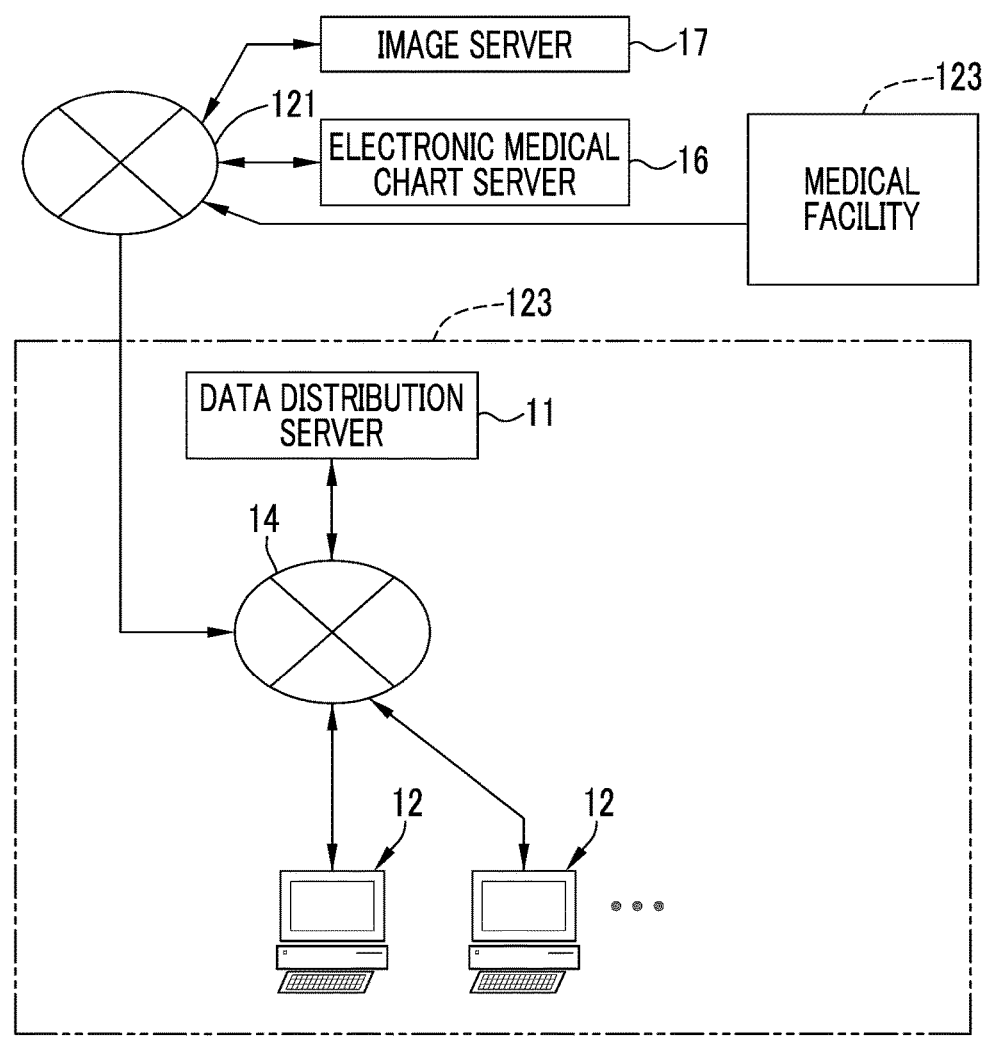
FIG. 29 is an illustrative diagram illustrating a configuration of a medical information system in which a data distribution server is arranged in a medical facility, and an electronic medical chart server and an inspection image server are arranged outside the medical facility.

Further, as illustrated in FIG. 28, the electronic medical chart server 16 or the image server 17 may be installed outside the medical facility 123. As illustrated in FIG. 29, the data distribution server 11 may be installed within the medical facility 123 and only the electronic medical chart server 16 or the image server 17 installed in the outside may be used.

It should be understood that the present invention is not limited to each embodiment and various configurations may be adopted as long as the configurations depart from the gist of the present invention. For example, various embodiments or various modification examples described above may be appropriately combined. Further, the present invention includes a storage medium that stores the program, in addition to the program.

What is claimed is:

1. A data output device for displaying time-series data indicating at least one of a state transition of a patient or content of medical care performed on the patient, the data output device comprising:
    a processor configured to perform the functions of:
    generating screen data of a data display screen including a first display area for displaying the time-series data, and a second display area for displaying a time axis in a time scale relatively longer than that of the first display area;
    receiving an indicator assignment instruction to assign a first indicator to a designated position designated on the time-series data; and
    assigning the first indicator at the designated position in the first display area on the basis of the indicator assignment instruction, and assigns a second indicator indicating that there is the first indicator to a corresponding position that temporally corresponds to the designated position in the second display area,
    wherein the data display screen includes a list display area for displaying content of a plurality of first indicators as a list, in addition to the first display area and the second display area,
    wherein the first indicator is associated with an attribute of the time-series data to which the first indicator is assigned, and
    wherein in the list display area, the first indicators to be displayed are narrowed down from among the plurality of first indicators according to the attribute.

2. The data output device according to claim 1, wherein the processor is configured to further perform the functions of:
    setting a degree of importance for at least one of the first indicator or the second indicator; and
    changing a display mode of at least one of the first indicator or the second indicator according to the setting of the degree of importance.

3. The data output device according to claim 1, wherein in the data display screen, in the event that one of the second indicators displayed in the second display area is selected, a first display period of the first display area is able to be changed to a display period including the first indicator corresponding to the selected second indicator.

4. The data output device according to claim 1, wherein in the data display screen, a second display period of the second display area is able to be set according to a period in which there is the first indicator.

5. The data output device according to claim 4, wherein in the data display screen, a period in which there is the first indicator is extracted from a most recent predetermined period, and the second display period is set.

6. The data output device according to claim 1, wherein the first indicator is a tag in which text is able to be displayed.

7. The data output device according to claim 1, wherein only the first indicator displayed in the list display area is displayed in the first display area.

8. The data output device according to claim 1, wherein the time-series data includes at least one of data regarding a vital sign including at least one of a heart rate, a pulse rate, blood pressure, body temperature, or respiration, data regarding inspection, or data regarding treatment.

9. The data output device according to claim 8, wherein the data regarding the inspection includes an inspection value expressed as a numerical value, or an inspection image, and
    the data on treatment includes administration content of a drug.

10. The data output device according to claim 1, wherein in the first display area, a plurality of pieces of time-series data is able to be displayed.

11. The data output device according to claim 1, wherein in the first display area, a display form of the time-series data is a graph or a table.

12. The data output device according to claim 1, wherein in the second display area, a data presence indicator indicating a data presence period in which there is time-series data is displayed along a time axis.

13. A data output method for displaying time-series data indicating at least one of a state transition of a patient or content of medical care performed on the patient on a display unit, the data output method comprising:
    a screen data generation step of generating screen data of a data display screen including a first display area for displaying the time-series data, and a second display area for displaying a time axis in a time scale relatively longer than that of the first display area;
    an indicator assignment instruction reception step of receiving an indicator assignment instruction to assign a first indicator to a designated position designated on the time-series data; and
    an indicator assignment step of assigning the first indicator to the designated position in the first display area on the basis of the indicator assignment instruction, and assigning a second indicator indicating that there is the first indicator to a corresponding position that temporally corresponds to the designated position in the second display area, wherein the data display screen includes a list display area for displaying content of a plurality of first indicators as a list, in addition to the first display area and the second display area, wherein the first indicator is associated with an attribute of the time-series data to which the first indicator is assigned, and wherein in the list display area, the first indicators to be displayed are narrowed down from among the plurality of first indicators according to the attribute.

14. A non-transitory computer readable medium for storing a computer-executable program enabling execution of computer instructions to perform operations for displaying time-series data indicating at least one of a state transition of a patient or content of medical care performed on the patient on a display unit, said operations comprising:

generating screen data of a data display screen including a first display area for displaying the time-series data, and a second display area for displaying a time axis in a time scale relatively longer than that of the first display area;

receiving an indicator assignment instruction to assign a first indicator to a designated position designated on the time-series data; and assigning the first indicator to the designated position in the first display area on the basis of the indicator assignment instruction, and assigning a second indicator indicating that there is the first indicator to a corresponding position that temporally corresponds to the designated position in the second display area, wherein the data display screen includes a list display area for displaying content of a plurality of first indicators as a list, in addition to the first display area and the second display area, wherein the first indicator is associated with an attribute of the time-series data to which the first indicator is assigned, and wherein in the list display area, the first indicators to be displayed are narrowed down from among the plurality of first indicators according to the attribute.

* * * * *